(12) United States Patent
Gupta

(10) Patent No.: US 8,218,143 B2
(45) Date of Patent: Jul. 10, 2012

(54) NONINVASIVE DETECTION OF ELEMENTS AND/OR CHEMICALS IN BIOLOGICAL MATTER

(75) Inventor: Neelam Gupta, Bethesda, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 311 days.

(21) Appl. No.: 12/687,469

(22) Filed: Jan. 14, 2010

(65) Prior Publication Data
US 2010/0185067 A1 Jul. 22, 2010

Related U.S. Application Data

(63) Continuation-in-part of application No. 11/239,460, filed on Sep. 26, 2005, now Pat. No. 7,733,484.

(60) Provisional application No. 61/145,252, filed on Jan. 16, 2009.

(51) Int. Cl.
*G01J 3/28* (2006.01)
(52) U.S. Cl. ......... 356/326; 356/328; 600/310; 600/323
(58) Field of Classification Search .................. 356/326, 356/328; 600/310, 323, 476
See application file for complete search history.

(56) References Cited

U.S. PATENT DOCUMENTS

| | | | |
|---|---|---|---|
| 4,705,396 A | 11/1987 | Bergstrom | |
| 5,120,961 A | 6/1992 | Levin et al. | |
| 5,734,931 A | 3/1998 | Inoue et al. | |
| RE36,529 E | 1/2000 | Lewis et al. | |
| 6,485,150 B1 | 11/2002 | Driggers et al. | |
| 6,490,075 B1 | 12/2002 | Scheps et al. | |
| 6,750,964 B2 * | 6/2004 | Levenson et al. | 356/326 |
| 7,106,435 B2 | 9/2006 | Nelson | |
| 7,141,786 B2 | 11/2006 | McGan et al. | |
| 7,147,153 B2 * | 12/2006 | Rowe et al. | 235/382 |
| 7,199,876 B2 | 4/2007 | Mitchell | |
| 7,535,617 B2 | 5/2009 | Gupta et al. | |
| 7,949,387 B2 * | 5/2011 | Khoobehi et al. | 600/476 |
| 2001/0052979 A1 | 12/2001 | Treado et al. | |
| 2002/0052979 A1 | 5/2002 | Kappel et al. | |
| 2002/0057431 A1 | 5/2002 | Fateley et al. | |

(Continued)

OTHER PUBLICATIONS

Gupta, et al.,"Object Detection with a Field-portable Spectropolarimetric Imager," Applied Optics, vol. 40, Issue 36, pp. 6626-6632 doi:10.1364/AO.40.006626 Dec. 2001.

(Continued)

*Primary Examiner* — Layla Lauchman
(74) *Attorney, Agent, or Firm* — Lawrence E. Anderson

(57) ABSTRACT

A method of detecting oxygen and/or chemical content in a subject, comprising generating at least one spectral image of the subject; generating at least one spectral image of a reference object; comparing spectrum from the subject image to the reference image to thereby reveal the relative oxygen content of the subject. A system for determining the level of oxygenation of the blood of a subject body part comprising: a hyperspectral image generator for generating a plurality of spectral images; an image capture device for capturing the spectral images; a processor for generating hyperspectral image cubes such that the spectrum of the body part is extracted and normalized using the spectrum from the reference object to cancel out the spectral response of the light source and the imager; said processor comparing spectral from a subject image to reference images to thereby reveal the relative oxygen content of the subject.

17 Claims, 16 Drawing Sheets

U.S. PATENT DOCUMENTS

| | | | |
|---|---|---|---|
| 2004/0021861 A1* | 2/2004 | Lewis et al. | 356/326 |
| 2007/0024946 A1* | 2/2007 | Panasyuk et al. | 359/253 |
| 2007/0038042 A1* | 2/2007 | Freeman et al. | 600/310 |

OTHER PUBLICATIONS

"Design and Fabrication of Acousto-Optic Devices," Chap. 4 in Designing and Fabrication of Acousto-Optic Devices, A. Goutzoulis and D. Pape, Eds., pp. 197-283, Marcel Dekker, New York: (1994).

"Stokes polarimetry using liquid crystal variable retarders," Meadowlark Optics, Inc. (2005). URL http://www.meadowlark.com.

N. Kollias,"Quantitative assessment of UV-induced pigmentation and erythema," Photodermatol. 1988; 5, pp. 53-60.

M.P. Siegel, et al., "Assessment of blood supply in superficial tissue by polarization-gated eleastic light-scattering spectroscopy," 45, Appl. Optics, 2006.

Scott Prahl,"Optical Absorption of Hemoglobin" Oregon Medical Laser Center, http://omlc.ogi.edu/spectra/ hemoglobin/, Dec. 1999.

N. Gupta, "Biosensors Technologies-Acousto-Optic Tunable Filter based Hyperspectral and Polarization Imagers for Fluorescence and Spectroscopic Imaging," in "Methods in Biotechnology," edited by Avraham Rasooly and Keith E. Herold by the Humana Press Inc., Totowa, NJ, p. 293-305, Nov. 2008.

W. R. Johnson, et al. "Snapshot hyperspectral imaging in ophthalmology," J. Biomed. Opt., 12, 14036-14043, (2007).

J. C. Ramella-Roman, S. A. Mathews, "Spectroscopic Measurements of Oxygen Saturation in the Retina," (IEEE J. of Selected Topics in Quantum Electronics 13, 1697-1703, 2007).

M. Sova, et al. "Near Infrared spectroscopic assessment of hemodynamic changes in the early post-burn period," Burns 27, 241-249 (2001).

M. Hassan, et al. "Quantitative assessment of tumor vasculature and response to therapy in kaposi's sarcoma using functional noninvasive imaging," Technol. Cancer Res. Treat. 3(5), 451-457 (2004)).

N. Gupta, et al. "Progress in AOTF Hyperspectral Imagers," in Automated Geo-Spatial Image and Data Exploitation, W. E. Roper and M. K. Hamilton, Eds., Proc. SPIE 4054, 30-38, (2000).

N. Gupta, et al. "Object detection using a fieldportable spectropolarimetric imager," App. Opt.40, 6626-6632 (2001).

N. Gupta, et al. "Acousto-optic tunable filter based visible-to-near-infrared spectropolarimetric imager," Opt. Eng. 41, 1033-1038 (2002).

N. Gupta, and V. Voloshinov, "Hyperspectral Imager from Ultraviolet to Visible Using KDP AOTF," Appl. Opt. 43, 2752-2759 (2004).

N. Gupta, "Acousto-optic tunable filters for Infrared Imaging," Proc SPIE 5953, 59530O 1-10 (2005).

N. Gupta, "Acousto-Optic Tunable Filter-based Spectropolarimetric Imagers for Medical Diagnostic Applications—Instrument Design Point of View," Journal of Biomedical Optics (JBO), 10, 051802-1-6 (2005).

N. Gupta and D. R. Suhre, "AOTF imaging spectrometer with full Stokes polarimetric capability," Appl. Opt. 46, 2632-2037 (2007).

Gottlieb, M. S., "Acousto-optic tunable filter," Design and Fabrication of Acousto-Optic Devices, A. P. Goutzoulis and D. R. Pape, eds., Marcel Dekker, New York, 1994, pp. 197-283.

Gupta, N., ed., Proceedings of the First Army Research Laboratory Acousto-Optic Tunable Filter Workshop, Army Research Laboratory, ARL-SR-54 (1997).

Gupta, N. and Fell, N. F., Jr., "A compact collinear Raman spectrometer," Talanta 45, 279-284 (1997).

Tran, "Acousto-Optic Devices Optical Elements for Spectroscopy" Analytical Chemistry, vol. 64, No. 20, 971A-981A.

Kwon, et al., Adaptive anomaly detection using subspace separation for hyperspectral imagery, Opt. Eng. 42(11) 3342-3351 (Nov. 2003).

N. Gupta and R. Dahmh, "Acousto-Optic Sensing and Imaging for Biomedical Applications," Proceedings—19th International Conference—IEEE/EMBS Oct. 30-Nov. 2, 1997 Chicago, IL. USA.

Gupta, N., "Acousto-Optic Tunable Filters" Optics & Photonics News/Nov. 1997, pp. 23-27.

Bennett & Gupta, et al. "Development of In-House Grating Spectrometer System for Validating Acousto-Optic Tunable Fileter Spectrometer Results," ARL MR-495 Mar. 2001.

Kwon, Heesung Rosario, Dalton Gupta, Neelam Thielke, Matthew, et al. "Hyperspectral Imaging and Obstacle Detection for Robotics Navigation," Army Research Lab Adelphi MD Sensors and Electron Devices DI..Source Code: 434660, 80 page(s),AD Number: ADA486436Report Date: Sep. 1, 2005.

* cited by examiner

FIGURE 6 AOTF Spectropolarimetric Imagers

| Imager | Spectral Range (μm) | Spectral Resolution (nm) | AOTF Material | Cell FOV ° | Retarder | FPA |
|---|---|---|---|---|---|---|
| UV | 0.20-0.48 | 1.4@0.3 μm | KDP MgF$_2$ | 1.2 | | Si-CCD 640x480 Uncooled |
| VNIR | 0.4-0.8 | 10 @0.6 μm | TeO$_2$ | 4 | Nematic LC | Si-CCD 640x480 Uncooled |
| SWIR | 0.9-1.7 | 10.4 @1.3 μm | TeO$_2$ | 8.4 | " | InGaAs 320x240 Uncooled |
| MWIR | 2.0-4.5 | 77@ 3 μm | TeO$_2$ | 3 | " | InSb 256x256 LN$_2$-cooled |
| LWIR | 7.8-10.5 | 80 @ 10 μm | TAS | 7.75 | | HgCdTe 256x256 LN$_2$-cooled |

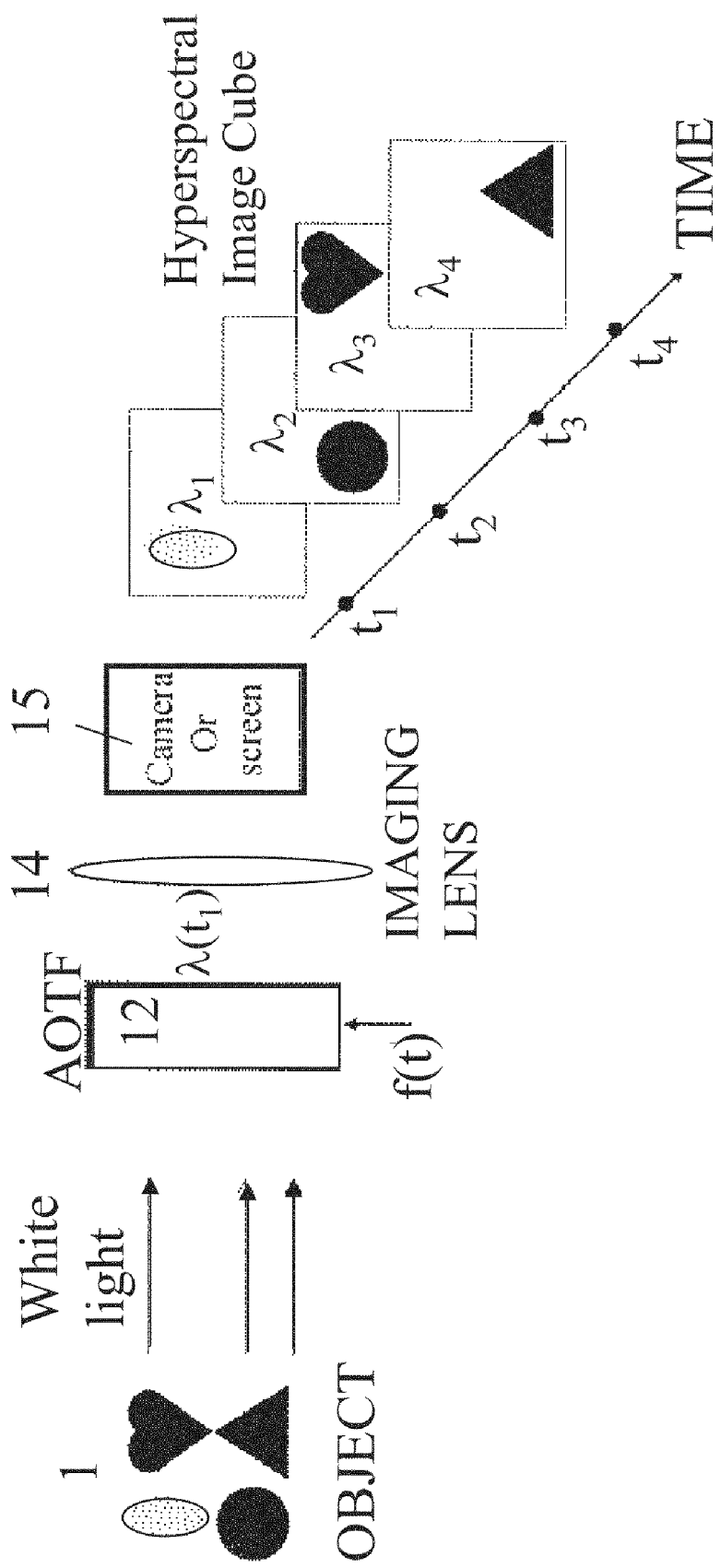

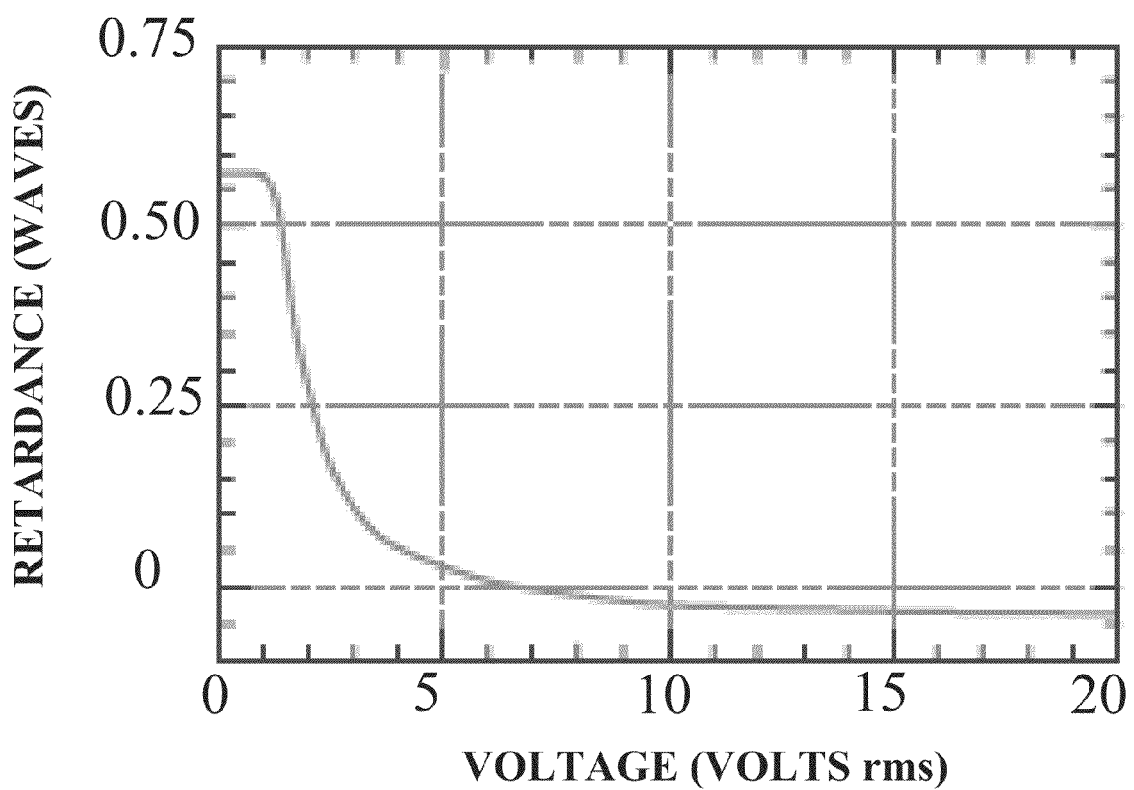
FIGURE 8     Retarder Tuning curve

FIGURE 10 RAW SPECTRAL IMAGES OF HAND AND ARM WITH HORIZONTAL POLARIZATION
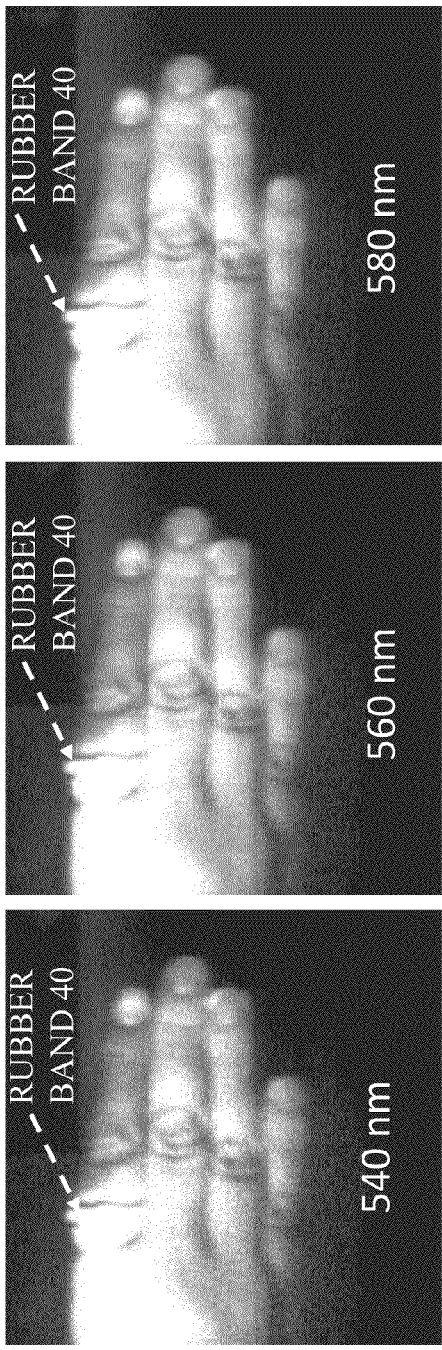
Hand with constricted index finger
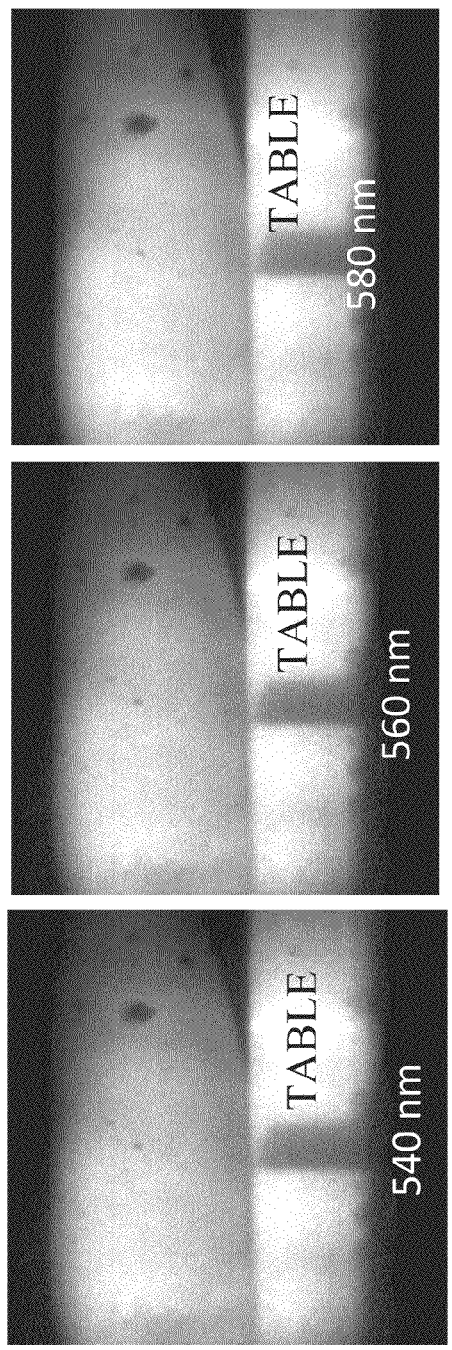
Lower arm resting on table with constricted upper arm (partial view)

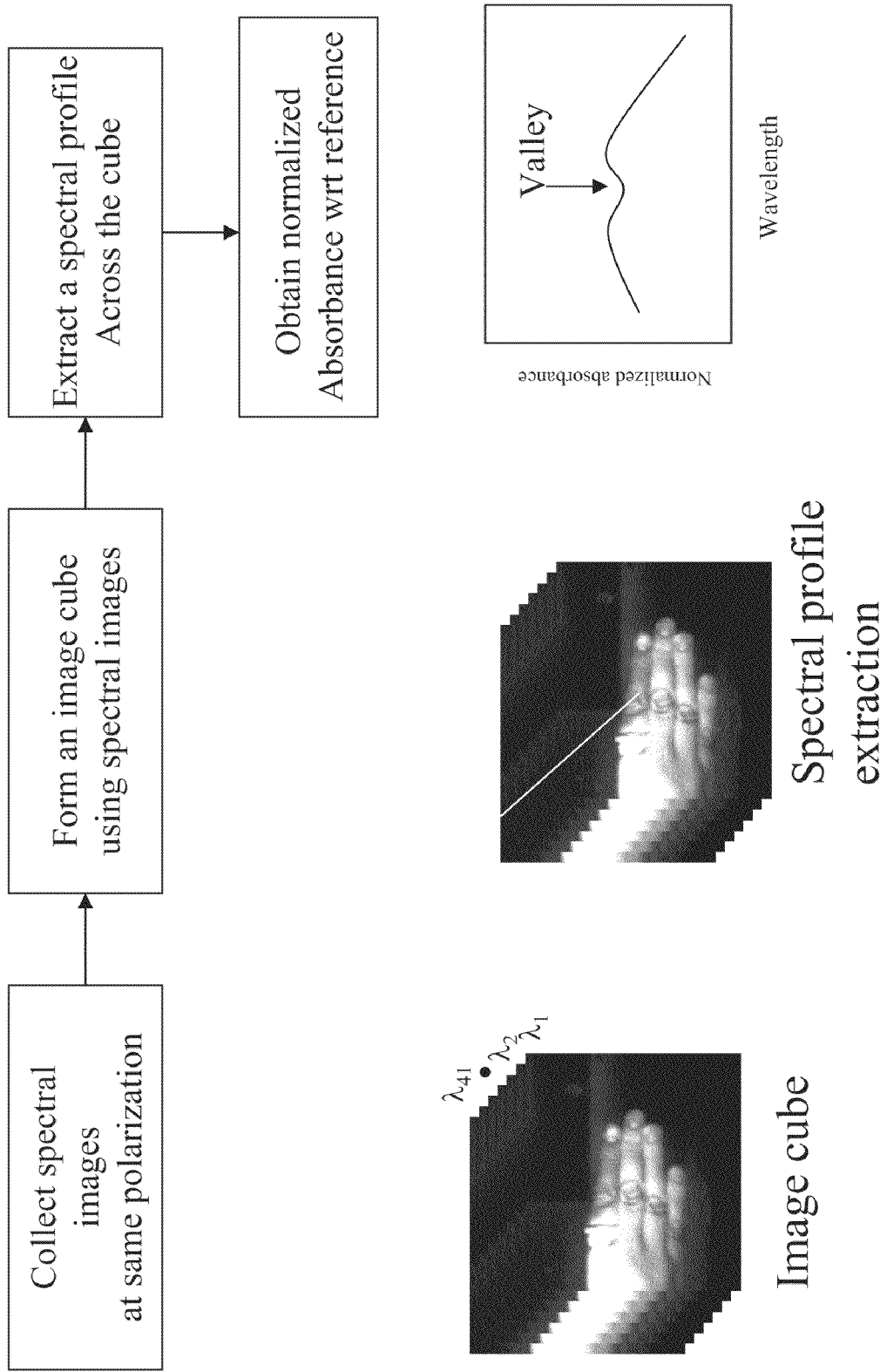
FIGURE 11 Image Acquisition & Analysis

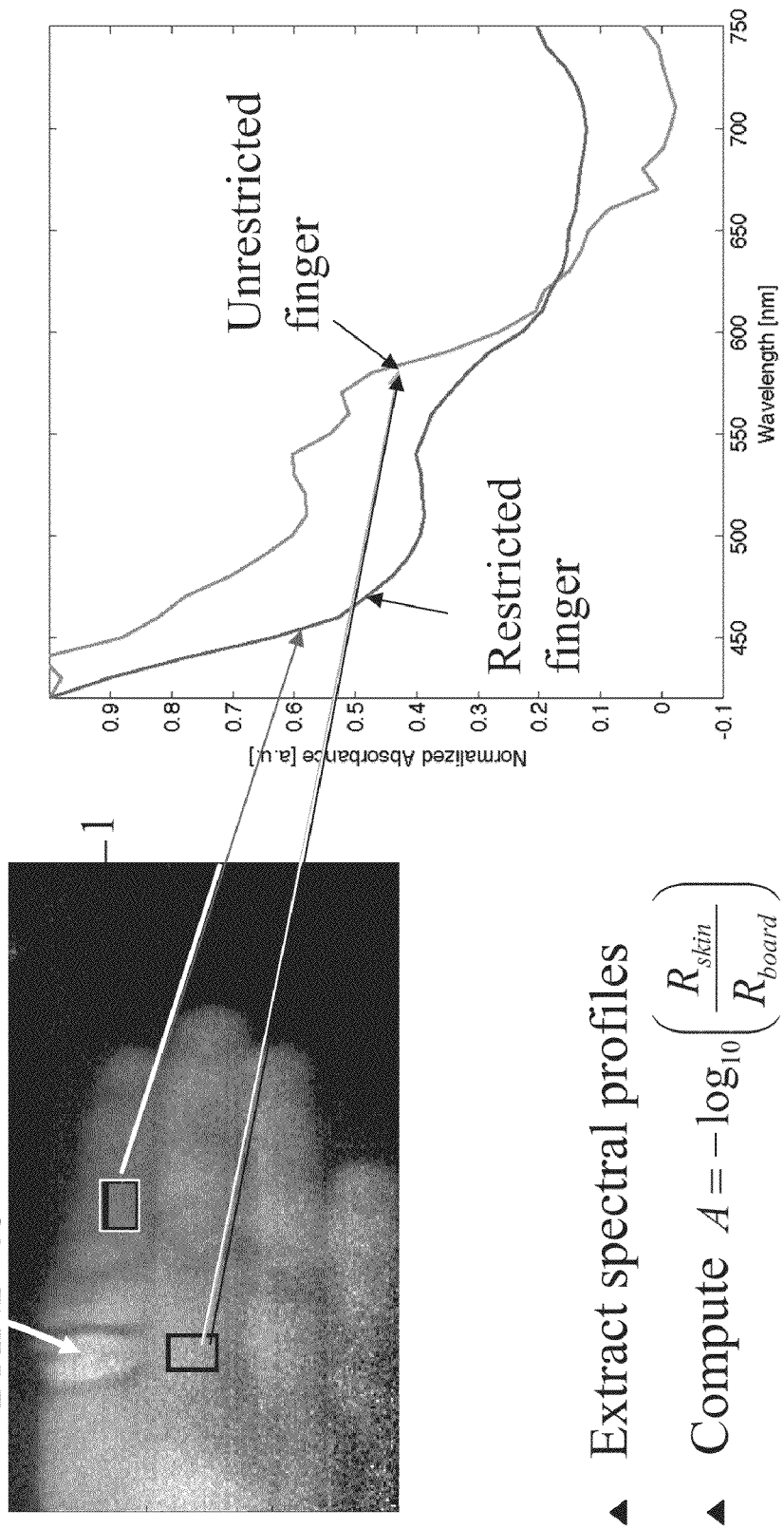
FIGURE 12 Skin Oxigenation Analysis

FIGURE 13 Normalized Spectral Absorbance
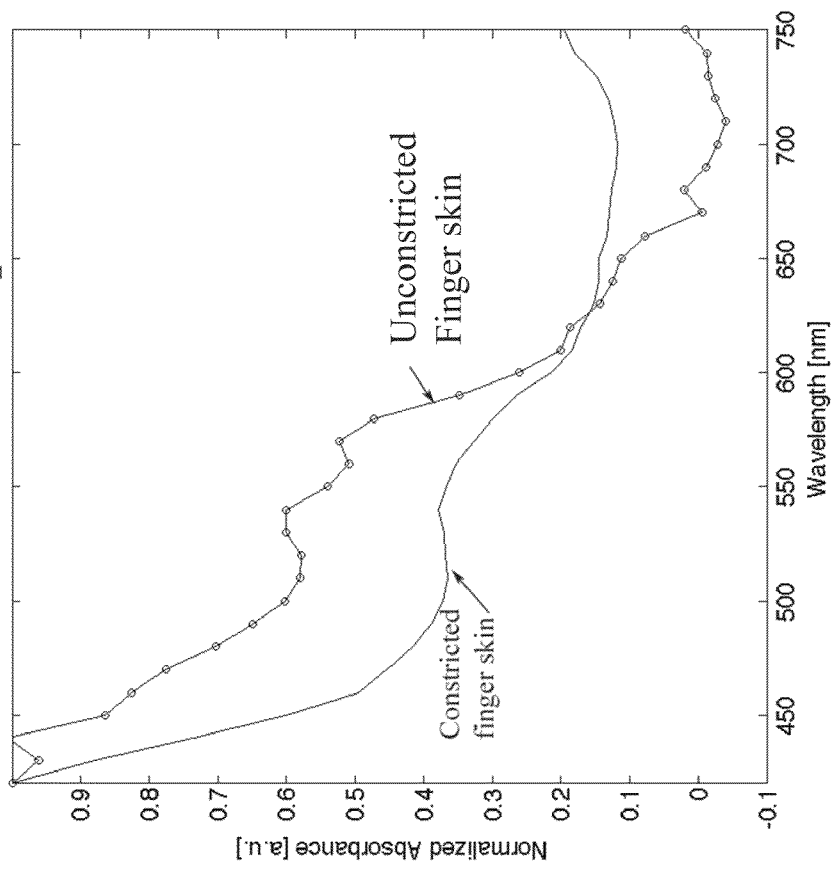
Absorbance spectrum for unconstricted finger typical of oxygenated hemoglobin with 2 visible peaks at 540 nm and 577 nm; for constricted finger these peaks disappear, a single large peak centered @ 559 nm for deoxyhemoglobin appears.

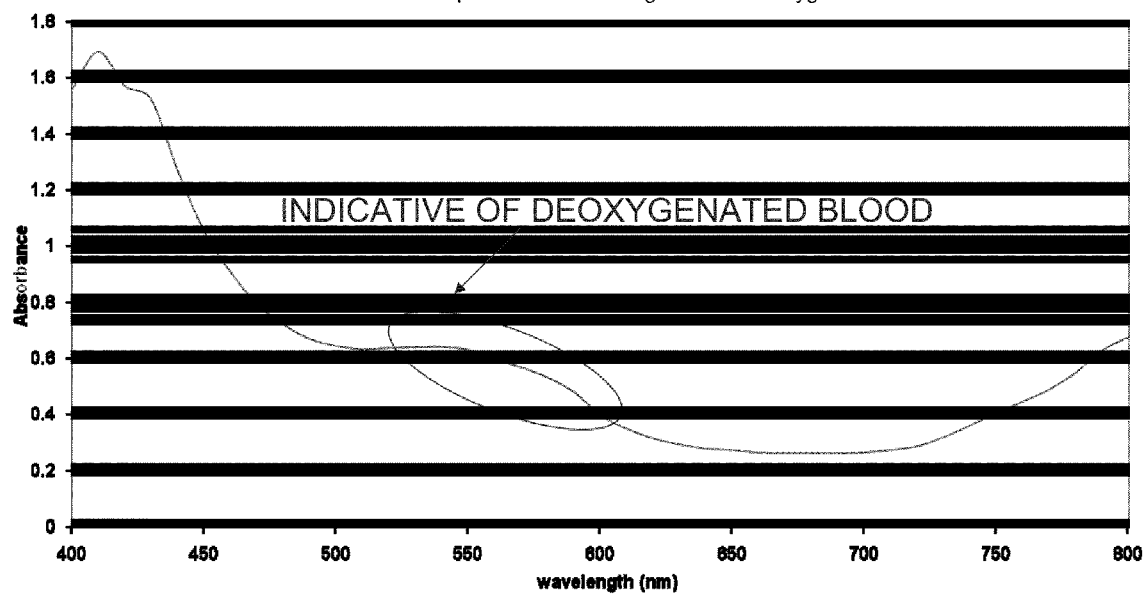
FIGURE 15 Plot of spectral absorbance of index finger with rubber band using image cube with horizontal polarization showing effect of deoxygenated blood.

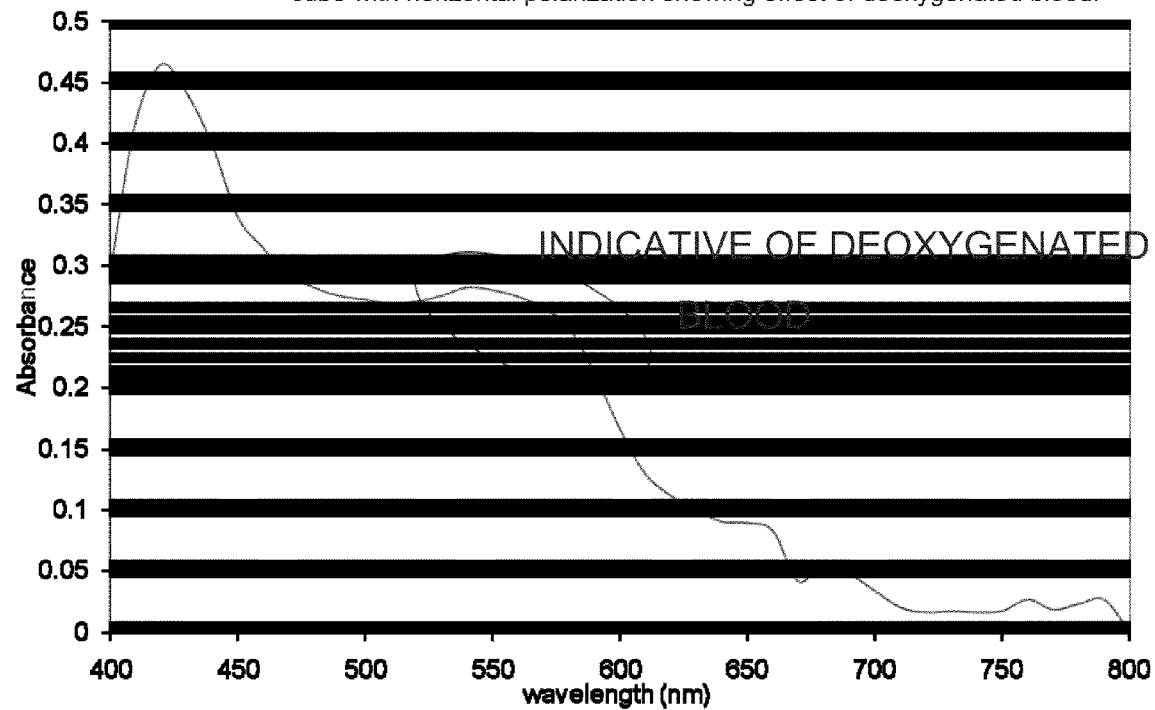
FIGURE 16 Plot of spectral absorbance of arm with pressure cuff using image cube with horizontal polarization showing effect of deoxygenated blood.

NONINVASIVE DETECTION OF ELEMENTS AND/OR CHEMICALS IN BIOLOGICAL MATTER

CROSS REFERENCE TO RELATED APPLICATIONS

This application is a continuation-in-part of U.S. application Ser. No. 11/239,460 filed Sep. 26, 2005, by Dr. Neelam Gupta, entitled HYPERSPECTRAL SCENE PROJECTION/ GENERATION SYSTEMS AND METHODS, ARL 04-67, which is hereby incorporated by reference as though fully rewritten herein. This application also claims priority to U.S. Provisional Application No. 61/145,252, filed Jan. 16, 2009, hereby incorporated by reference as though fully rewritten herein.

STATEMENT OF GOVERNMENT INTEREST

The invention described herein may be manufactured, used, and licensed by or for the United States Government.

FIELD OF THE INVENTION

This invention relates broadly to spectral imaging and specifically to noninvasive detection of elements and/or chemicals in biological matter.

BACKGROUND OF THE INVENTION

Hyperspectral imaging collects and processes information from across the electromagnetic spectrum. Hyperspectral imaging may utilize light in the electromagnetic spectrum ranging from ultraviolet to infrared light. Hyperspectral capabilities enable the recognition of different types of organisms, all which may appear as the same color to the human eye. Hyperspectral sensors differentiate objects based upon unique "fingerprints" across the electromagnetic spectrum that are known as spectral signatures and enable identification of the materials that make up a scanned object. Hyperspectral sensors collect information as a set of "images" with each image representing a range of the electromagnetic spectrum, also known as a spectral band. Such "images" may be combined to form a three dimensional hyperspectral cube for processing and analysis.

Spectroscopic imagers have been developed for a variety of biomedical applications, from retinal oximeters (see W. R. Johnson, D. W. Wilson, W. Fink, M. Humayun, and G. Bearman, "Snapshot hyperspectral imaging in opthalmology," J. Biomed. Opt., 12, 14036-14043, (2007) and J. C. Ramella-Roman, S. A. Mathews, "Spectroscopic Measurements of Oxygen Saturation in the Retina," (IEEE J. of Selected Topics in Quantum Electronics 13, 1697-1703, 2007) to evaluation of skin burn depths (see M. Soya, L. Leonardi, J. Payette, J. Fish, H. Mantsch, "Near Infrared spectroscopic assessment of hemodynamic changes in the early post-burn period," Burns 27, 241-249 (2001) and evaluation of skin lesions (see, e.g., M. Hassan, R. Little, A. Vogel, K. Aleman, K. Wyvill, R. Yarchoan, and A. Gandjbakhche, "Quantitative assessment of tumor vasculature and response to therapy in kaposi's sarcoma using functional noninvasive imaging," Technol. Cancer Res. Treat. 3(5), 451-457 (2004)).

Depending on the application, spectroscopic imagers are completely passive (as disclosed in W. R. Johnson, D. W. Wilson, W. Fink, M. Humayun, and G. Bearman, "Snapshot hyperspectral imaging in opthalmology," J. Biomed. Opt., 12, 14036-14043, (2007) and J. C. Ramella-Roman, S. A. Mathews, "Spectroscopic Measurements of Oxygen Saturation in the Retina," (IEEE J. of Selected Topics in Quantum Electronics 13, 1697-1703, 2007) or are able to switch through different wavelengths by tuning a wavelength dependent apparatus, as in the case for Liquid Crystals Tunable Filters (LCTF) and Acoustic Optics Tunable Filters (AOTF). Compact hyperspectral imagers based on AOTF have been developed at the Army Research Laboratory. Reports on the same are in publications N. Gupta, R. Dahmani, and K. Bennett, S. Simizu, D. R. Suhre, and N. B. Singh, "Progress in AOTF Hyperspectral Imagers," in Automated Geo-Spatial Image and Data Exploitation, W. E. Roper and M. K. Hamilton, Eds., Proc. SPIE 4054, 30-38, (2000); N. Gupta, L. Denes, M. Gottlieb, D. Suhre, B. Kaminsky, and P. Metes, "Object detection using a fieldportable spectropolarimetric imager," App. Opt. 40, 6626-6632 (2001); N. Gupta, R. Dahmani, and S. Choy, "Acousto-optic tunable filter based visible-to near-infrared spectropolarimetric imager," Opt. Eng. 41, 1033-1038 (2002); 8. N. Gupta, and V. Voloshinov, "Hyperspectral Imager from Ultraviolet to Visible Using KDP AOTF," Appl. Opt. 43, 2752-2759 (2004); N. Gupta, "Acousto-optic tunable filters for Infrared Imaging," Proc SPIE 5953, 59530O 1-10 (2005); N. Gupta, "Acousto-Optic Tunable Filter-based Spectropolarimetric Imagers for Medical Diagnostic Applications—Instrument Design Point of View," Journal of Biomedical Optics (JBO), 10, 051802-1-6 (2005); N. Gupta and D. R. Suhre, "AOTF imaging spectrometer with full Stokes polarimetric capability," Appl. Opt. 46, 2632-2037 (2007).

A number of hyperspectral imagers were built covering different spectral regions from the ultraviolet (UV) to the longwave infrared (LWIR). Such imagers can collect data at the wavelengths of interest, which is critical for hyperspectral applications because it greatly reduces the data processing requirements associated with traditional hyperspectral imaging systems using gratings and prisms where images are acquired in hundreds of bands without much flexibility. Optical tunable filter (OTF) imagers can switch among wavelengths in tens of micro-seconds, much faster than liquid crystal tunable filters (LCTF) that have 50 to 500 ms operating time. Unlike a traditional grating, prism or LCTF an acousto-optic tunable filter (AOTF) is also a polarization sensitive device because the diffracted beams from it are orthogonally polarized. By combining the AOTF with a spectrally tunable retarder to change the polarization of incident light on the imaging system, polarization information from the scene or subject of interest can also be obtained.

Portable Acousto-optical Spectrometers are disclosed in U.S. application Ser. No. 11/208,123, filed Aug. 18, 2005, which issued on May 19, 2009, as U.S. Pat. No. 7,535,617 to Gupta, et al, which is hereby incorporated by reference as though fully rewritten herein. As disclosed in U.S. Pat. No. 7,535,617, the AOTF is a birefringent crystal having an acoustic transducer bonded to one face. Broad-band light radiation passing through a crystal can be diffracted into specific wavelengths by application of a radio-frequency (rf) driving signal to the crystal transducer. Among the attractive features of AOTFs are their small size, light-weight, computer-controlled operation, large wavelength tuning range, and reasonably high spectral resolution. Additionally, their operation can be made ultra-sensitive by using advanced signal-processing algorithm.

A number of different crystals, i.e., quartz, LiNbO3, etc., allow collinear diffraction of light with either longitudinal or shear acoustic wave propagation. Chang generalized the design of an AOTF cell by introducing the concept of a noncollinear AOTF using tellurium dioxide ($TeO_2$), a birefringent crystal (a crystal having two refractive indices) that cannot exhibit collinear interaction because of its crystal symmetry. In a noncollinear AOTF cell the incident light, the diffracted light, and the acoustic wave do not travel in the same direction.

An AOTF is essentially a real-time programmable filter whose operation can be described as follows. When white light is incident on the filter, it passes only a selected number of narrow bands corresponding to the applied rf-signals. The filter can be used to pass light with either a single wavelength or multiple wavelengths, depending upon the number of applied rf-signals. Either a collinear or a non-collinear geometry can be used in designing an AOTF cell, based on the symmetry properties of the anisotropic crystal under consideration. The incident light is linearly polarized by a polarizer in front of the crystal before it enters the AOTF cell. As this polarized light passes through the cell, it is diffracted in the same direction by a diffraction grating set up by the collinearly traveling sound wave. Owing to conservation of energy, the frequency of the diffracted light is Doppler shifted, but this frequency shift is insignificant and can be ignored. Based on conservation of momentum, a tuning relationship can establish between the center wavelength of the filter and the applied rf-signal. Many excellent review articles on AOTF technology and applications are available, for example see Gottlieb, M. S., "Acousto-optic tunable filter," Design and Fabrication of Acousto-Optic Devices, A. P. Goutzoulis and D. R. Pape, eds., Marcel Dekker, New York, 1994, pp. 197-283; Gupta, N., ed., Proceedings of the First Army Research Laboratory Acousto-Optic Tunable Filter Workshop, Army Research Laboratory, ARL-SR-54 (1997); and Gupta, N. and Fell, N. F., Jr., "A compact collinear Raman spectrometer," Talanta 45, 279-284 (1997). A more complete description is found at N. Gupta, "Biosensors Technologies-Acousto-Optic Tunable Filter based Hyperspectral and Polarization Imagers for Fluorescence and Spectroscopic Imaging," in "Methods in Biotechnology," edited by Avraham Rasooly and Keith E. Herold by the Humana Press Inc., Totowa, N.J., page 293-305, (November 2008).

An example of a spectrometer using AO crystal cells is found in U.S. Pat. No. 5,120,961 entitled "High sensitivity acousto-optic tunable filter spectrometer," hereby incorporated by reference, which teaches of using an acousto-optical filter (AOTF) device in a spectrometer. This spectrometer operates by using continuous wave RF-excitation through the crystal, wherein the spectrometer provides control and modulation of the RF-source. Noise is minimized by a lock-in amplifier that demodulates the modulation frequency. Fiber optics are used to connect the crystal to the source, and the source to the detection system.

One AOTF-based imager operates from the visible to the near infrared (400-800 nm). See N. Gupta, R. Dahmani, and S. Choy, "Acousto-optic tunable filter based visible-to near-infrared spectropolarimetric imager," Opt. Eng. 41, 1033-1038 (2002), hereby incorporated by reference. This imager operates in a passive mode by detecting the light either reflected or transmitted by an object. By using an electronically tunable liquid crystal variable retarder (LCVR) as a function of wavelength in the path of the incident light on the AOTF, the imagers are shown to detect both spectral and polarization signatures. In the article, a compact, lightweight, robust, and field-portable spectropolarimetric imager is developed to acquire spectropolarimetric images both in the laboratory and outdoors. The described imager used a tellurium dioxide (TeO2) acousto-optic tunable filter (AOTF) as an agile spectral selection element and a nematic liquid-crystal variable retardation (LCVR) plate as a tunable polarization selection device with an off-the-shelf chargecoupled device (CCD) camera and optics. The spectral range of operation was from 400 to 800 nm with a 10-nm spectral resolution at 600 nm. Each spectral image was acquired with two retardation values corresponding to the horizontal and vertical incident polarizations. The operation of the imager and image acquisition was computer controlled. For a further description of the instrument and its operation and present results of measurements, see the N. Gupta, et al., "Acousto-optic tunable filter based visible-to near-infrared spectropolarimetric imager," Opt. Eng. 41, 1033-1038 (2002), hereby incorporated by reference.

Turning to the medical field, currently an estimate of the oxygen saturation in the blood of a human body can be made with a clip that fits on the subject's finger. The clip operates by shining a light through the subject finger; and a detector measures the light that comes through the other side. The machine functions on the basis that oxygen saturated blood cells absorb and reflect light differently than those that are not. Blood cells are a bright red when they are loaded with oxygen, and they change to a bluish color when they are no longer carrying a full load. Such machines give only a rough estimate a body's oxygen saturation and its measurement can be affected such things as red nail polish on the finger. A more accurate test for measuring oxygen saturation of the blood is an arterial blood gas test; commonly obtained using a blood sample, however, such tests require the availability of the subject's blood and time for the analysis.

The measurement of the oxygen deficiency in the blood is an indicator of hypoxia oxygen deficiency, which occurs when there is an inadequate supply of oxygen to tissue. An inadequate supply of oxygen to tissue may be the result of a variety of factors, including an impairment or reduction in partial pressure of oxygen, inadequate oxygen transport, or the inability of the tissues to use oxygen. Reduction of the oxygen carrying capacity of the blood (or adequately oxygenated blood) due to circulation, liver, or heart disorders, causes tissue death. Conversely, oxygen deficiency in the body tissue is an indicator for disease, poisoning, and resulting death of tissue. Brain cells are extremely sensitive to oxygen deficiency and can begin to die within five minutes. Causative factors such as drowning, strangling, choking, suffocation, cardiac arrest, head trauma, and carbon monoxide poisoning can create conditions leading to cerebral hypoxia, which can lead to coma, seizures, and even brain death. Similarly, carbon monoxide and cyanide poisoning may lead to histotoxic hypoxia, which is the inability of body tissues to use oxygen. Also, certain narcotics will prevent oxygen use by the tissues. Conversely, lack of the presence of oxygen in body tissue may be indicative of poisoning, chemicals, or certain narcotic usage. Hypoxia may lead to a complete absence of oxygen in tissue or anoxia; a condition where the metabolism of cells is disrupted causing tissue cells to die within minutes.

In situations where common diagnostic procedures are not available or inadvisable to determine the medical condition of a human body, remote diagnosis (which does not involve human contact or contamination) based upon oxygen deficiency may be advantageous. Accordingly, there exists a need to determine blood oxygen content in body tissue without exposing others to potential diseases, biological agents, radiation hazards, or the causative factors of the oxygen deficiency. Since death may result within minutes of an extreme oxygen deficiency, a quick response time or diagnosis is not only highly desirable, but may be imperative.

SUMMARY OF INVENTION

A preferred embodiment of the present invention enables the detection of oxygen deficiency in the tissue of a human body or animal without the need for touch or bodily contact. One potential use is in situations where a subject body may have been exposed to a chemical or biological agent, or when it is inadvisable to touch the subject body. A preferred embodiment comprises a compact no-moving-parts wavelength-agile electronically-controlled hyperspectral/polarization imager using an acousto-optic tunable filter (AOTF) 12 with a liquid crystal variable retarder (LCVR) and a CCD camera. The AOTF imager can be used to passively sense a live human subject skin using, for example an unpolarized white light lamp source. The AOTF may be, for example, a polarization sensitive electronically tunable fast spectral filter. One of ordinary skill in the art could readily appreciate that the invention is not limited to the specific equipment used or to oxygen analysis. The equipment is usable in a noninvasive mode to passively image live human subject skin to detect oxygen (or chemical(s)) content in the blood. A preferred embodiment comprises an electrically tunable optical filter where a moving diffraction grating is set up in an anisotropic crystal by a propagating sound wave generated from an applied rf signal. In a noncollinear AOTF, incident light, sound and diffracted light beams propagate in different directions. For unpolarized incident white light, two orthogonally polarized and spatially separated diffracted beams with a narrow spectral bandwidth are generated for each rf. Response times may be on the order of ~tens of microsecond; much faster than LCTF.

Determination of whether a person's blood is oxygenated or deoxygenated is conducted using remotely captured hyperspectral images of a person's arm or other body parts obtained by an acousto-optic based hyperspectral imager operating from 400 to 800 nm. In accordance with a preferred methodology of the present invention, the light from a fiber optic coupled source is illuminated on a person's body part and then spectral images using the reflected light are captured using an automated hyperspectral imager. Next, the body part is put under pressure to reduce the oxygen level in the blood and spectral images are captured. For a reference object, a diffuse white board sitting at the same position as the body part is then imaged with same illumination. Hyperspectral image cubes are generated using a commercial hyperspectral software package and spectrum of a point on the body part (e.g., arm) may be extracted and normalized using the spectrum from the white board; effectively canceling out the spectral response of the light source and the imager. Observed spectra from a body part where the blood is deoxygenated is distinguishable from the body part under normal conditions; thereby revealing that the blood is oxygenated or deoxygenate. The present invention is particularly useful in an environmental or remote field scenario to remotely determine if a human is alive or dead without touching his or her body to determine the presence of a pulse. Further exposure of personnel to chemical and biological agents is thereby avoided if the subject in question was exposed to toxins in the environment. The AOTF-based imager can be utilized for biomedical applications in either hyperspectral or spectropolarimetric modes.

These and other aspects of the embodiments of the invention will be better appreciated and understood when considered in conjunction with the following description and the accompanying drawings. It should be understood, however, that the following descriptions, while indicating preferred embodiments of the invention and numerous specific details thereof, are given by way of illustration and not of limitation. Many changes and modifications may be made within the scope of the embodiments of the invention without departing from the spirit thereof, and the embodiments of the invention include all such modifications.

BRIEF DESCRIPTION OF THE DRAWINGS

FIG. 2 illustrates the diffraction of beams.

FIG. 6 illustrates the specifications of various AOTF Spectropolarimetric imagers.

FIG. 7 schematically depicts the production of a hyperspectral image cube.

FIG. 8 is a graph of the retardance as a function of voltage for an LCVR 13, one of which is depicted in FIG. 5.

FIG. 10 shows three spectral images of a hand with one finger and an arm under pressure collected in the lab; collected with horizontal polarization. The top of FIG. 10 shows three examples of reflected spectral images of a human hand with only the index finger under constriction and the bottom shows similar images for lower arm with a pressure cuff on the upper arm (not shown) collected with horizontal polarization.

FIG. 11 is a flow diagram of the image acquisition process and analysis using a preferred embodiment of the present invention. Also illustrated are an image cube and spectral profile extraction.

FIG. 12 is an illustration of skin oxigenation analysis showing a graphical correlations representing constricted/restricted and nonconstricted/unrestricted fingers.

FIG. 13 is a graphical presentation illustrating a normalized spectral absorbance showing a comparison of constricted/restricted and nonconstricted/unrestricted finger skin.

FIG. 15 is a graphical illustration representing deoxygenated blood (arising from a rubber banded finger) with a spectral plot obtained from image cubes in which absorbance is plotted as a function of wavelength of light in nanometers (with horizontal polarization).

FIG. 16 is a graphical illustration representing deoxygenated blood (arising from a lower arm) with a spectral plot obtained from image cubes in which absorbance is plotted as a function of wavelength of light in nanometers (with horizontal polarization).

Figure 1:
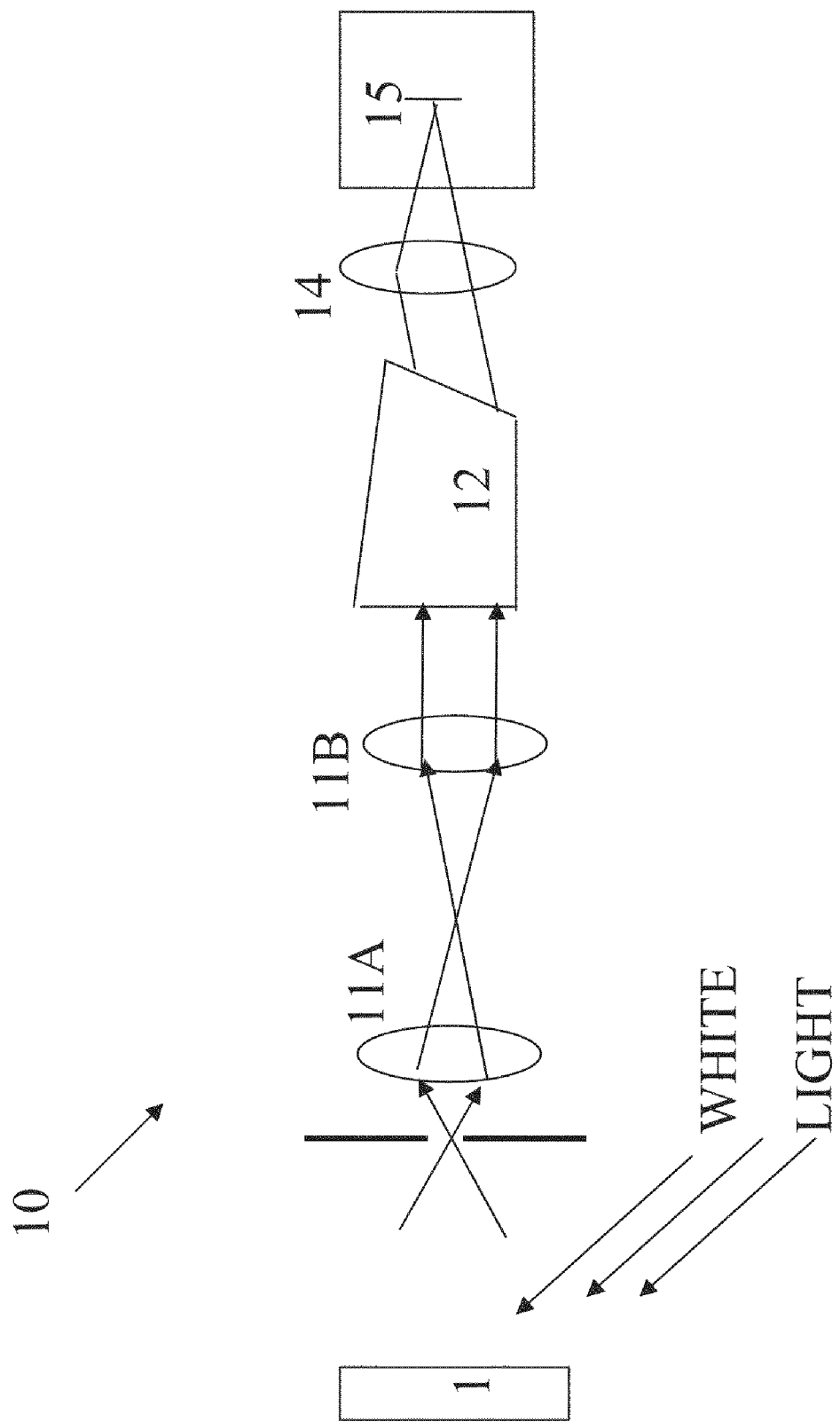
FIG. 1 is a schematic diagram of a hyperspectral imaging system showing the propagation of light and sound waves using an acousto-optic tunable filter (AOTF) imager.

A more complete appreciation of the invention will be readily obtained by reference to the following Description of the Preferred Embodiments and the accompanying drawings in which like numerals in different figures represent the same structures or elements. The representations in each of the figures are diagrammatic and no attempt is made to indicate actual scales or precise ratios. Proportional relationships are shown as approximates.

DESCRIPTION OF PREFERRED EMBODIMENTS

The embodiments of the invention and the various features and advantageous details thereof are explained more fully with reference to the non-limiting embodiments that are illustrated in the accompanying drawings and detailed in the following description. It should be noted that the features illustrated in the drawings are not necessarily drawn to scale. Descriptions of well-known components and processing techniques are omitted so as to not unnecessarily obscure the embodiments of the invention. The examples used herein are intended merely to facilitate an understanding of ways in which the embodiments of the invention may be practiced and to further enable those of skilled in the art to practice the embodiments of the invention. Accordingly, the examples should not be construed as limiting the scope of the embodiments of the invention.

The terminology used herein is for the purpose of describing particular embodiments only and is not intended to limit the full scope of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood that, although the terms first, second, etc. may be used herein to describe various elements, components, beams, layers and/or sections, these elements, components, beams, layers and/or sections should not be limited by these terms. For example, when referring first and second beams, these terms are only used to distinguish one beam from another. Thus, a first beam discussed below could be termed a second beam without departing from the teachings of the present invention.

Embodiments of the present invention are described herein with reference to cross-section illustrations that are schematic illustrations of idealized embodiments of the present invention. As such, variations from the shapes of the illustrations as a result, for example, of manufacturing techniques and/or tolerances, are to be expected. Thus, embodiments of the present invention should not be construed as limited to the particular shapes of regions illustrated herein but are to include deviations in shapes that result, for example, from manufacturing. For example, a region or object illustrated as a rectangular will, typically, have tapered, rounded or curved features. Thus, the regions illustrated in the figures are schematic in nature and their shapes are not intended to illustrate the precise shape of a region of a device and are not intended to limit the scope of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 2:
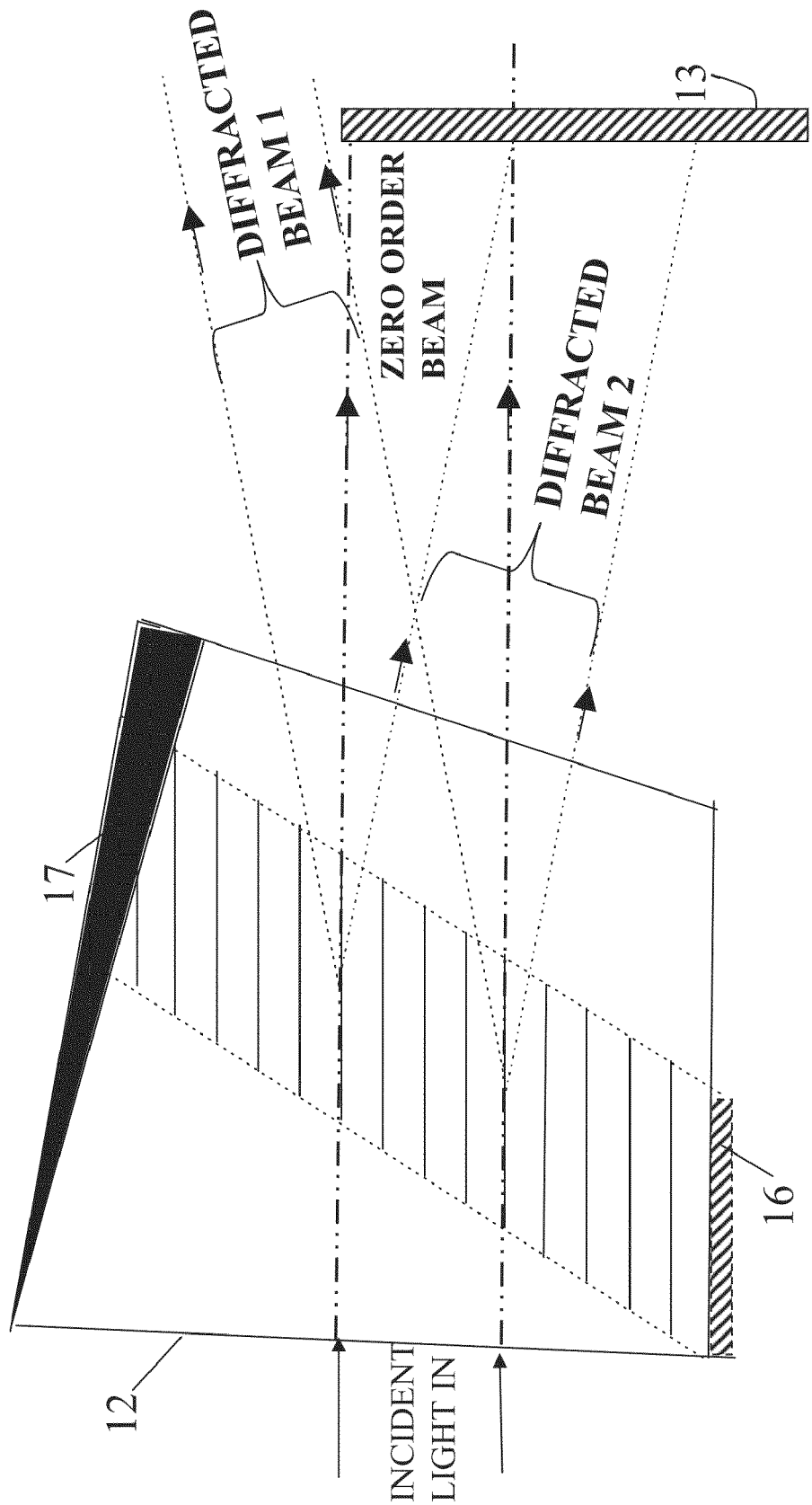
FIG. 2 is an enlarged schematic diagram of a spectral filtering operation using an acousto-optic tunable filter 12 (AOTF) is shown here with the transducer and absorber.

As illustrated in FIG. 1, the invention may be, for example, performed using an acousto-optic tunable filter (AOTF) 12 that uses radio waves to filter white light into different colors of diffracted light. As illustrated in FIG. 2, the AOTF 12 device is made up of a specially cut birefringent crystal prism on which a thin plate piezoelectric transducer 16 is bonded on one side of the crystal and an acoustic absorber 17 on the opposite facet. When a radio frequency wave is applied to this transducer, it generates an ultrasonic wave which travels through the crystal and gets absorbed at the other end by the acoustic absorber. The traveling sound wave in the crystal acts like a grating and light gets diffracted in an anisotropic diffraction process.

As shown in FIG. 1, the hyperspectral imaging system 10 comprises lenses 11A, B to collimate the light beam, an acousto-optic tunable filter 12, a lens 14 and a single color diffracted light camera 15. Although a camera is shown in FIG. 1, a charge coupled devices (CCD) operating as a spatially integrated detector could be used without departing from the spirit of the invention. Any array of detectors that covers an area or any detector that scans an area may be used in place of a CCD. Although lenses 11A, 11B and 14 have been described above, one of ordinary skill in the art would appreciate that the lenses could be omitted and/or replaces by suitable optical devices which provide for the focusing or redirecting of light such as prisms and the like.

There are two types of acousto-optic tunable filters (AOTF): collinear and non collinear. In a non collinear filter, incident and diffracted light and acoustic beams do not travel in the same direction while in a collinear filter all these beams travel in the same direction. As depicted in FIG. 2, for a white light collimated incident beam that is incident normal to the input facet of a noncollinear AOTF filter, in general there are three beams that come out of the crystal, two diffracted beams (1 and 2) and a zero order beam (as depicted by beams 303, 305 and 307, respectively, in FIG. 3). For a white light collimated incident beam that is incident normal to the input facet of a noncollinear filter, in general there are three beams that come out of the crystal. These include two diffracted beams at specific angles with respect to the incident beam with orthogonal polarization at a specific wavelength corresponding to the applied radio frequency and the third beam called the zero-order beam contain all the light except the amount that was diffracted at the particular optical wavelengths. As depicted in FIG. 2, the two diffracted beams are at specific angles with respect to the incident beam with orthogonal polarization at a specific wavelength corresponding to the applied radio frequency. The zero order beam contains the light remaining after the amount that was diffracted at the particular optical wavelengths.

In the case of a collinear filter where there is only one diffracted beam, a polarizer before the filter and an analyzer after the filter are used to separate the incident light and the zero order beam from the diffracted beam. The diffracted optical wavelength is inversely proportional to the applied radio frequency. The wavelength of the diffracted light can be changed by changing the applied radio frequency.

Acousto-optic tunable filters (AOTF) using $TeO_2$ crystal are available commercially covering wavelengths from 400 to 800 nm. The advantage of using such filters instead of traditional dispersive elements such as gratings and prism is that they can generate a full two dimensional scene at a specific wavelength at one time without using any motion. Also, wavelength can be changed in either a sequential or random manner. Another advantage of using such filters is fast speed; up to 100000 spectral frames per second can be generated. A third advantage is that no moving parts are involved and a robust system can be developed. A fourth advantage is that the frequency change operation can be done remotely. A fifth advantage is that spectral images can be captured only at desired wavelengths instead of generating hundreds of spectral scenes to fill the image cube. Other hyperspectral imagers using liquid crystal tunable filter, Fabry Perot tunable filters, diffractive optical lens and other techniques can also be used. The light source 2 can be a white light source such as a lamp or sunlight.

As depicted in FIG. 1, a preferred embodiment utilizes a fiber-optic coupled light as a source and an acousto optic tunable filter 12 to image different optical colors in the visible wavelength region. The acousto-optic tunable filter may be fabricated in single crystal of tellurium dioxide. Two plano-convex lenses 11A and 11B are used to form a collimated beam. The spectral scene is imaged on a commercial CCD camera 15 that is connected to a frame grabber to digitize the analog output of the camera. The digitized image is stored on a computer or image processor. The operation of the acousto-optic tunable filter (AOTF) 12 and camera 15 may be automated. The radio frequency signal applied to the imager is also controlled from the same software as the imager.

Figure 5:
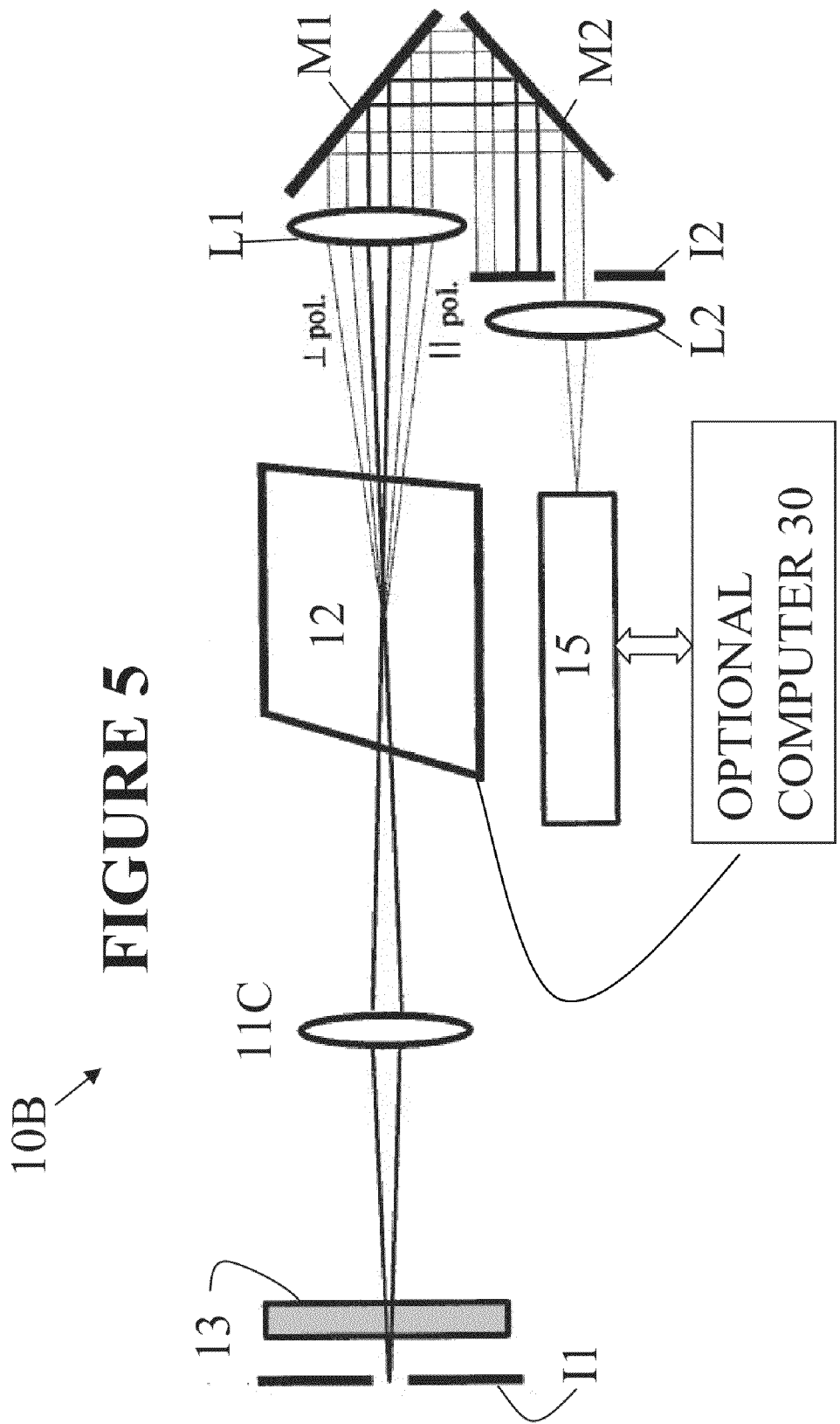
FIG. 5 is a diagrammatic illustration of a preferred embodiment hyperspectral imager using an acousto-optic tunable filter (AOTF) 12 for the light dispersive element in combination with LCVR 13 for polarization selection and a CCD camera to cover the spectral range of operation.

An AOTF imager used in conjunction with the principles of the present invention operates over the visible to near-infrared (VNIR) region from 400 to 800 nm. It has a 10 nm spectral resolution at 600 nm. Each spectral image is acquired with two retardation values from the liquid crystal variable retarder corresponding to the horizontal and vertical incident polarizations of light. The system (as shown in FIG. 5) comprises a tellurium dioxide ($TeO_2$) noncollinear AOTF, two irises (I1, I2), two plano-convex lenses L1, L2, two plane mirrors (M1,M2) mounted on adjustable tilt plates, an electronically tunable liquid crystal variable retarder (LCVR) 13, one camera lens 14 and one CCD camera 15. An optional computer 30 may be used to control the assembly and for storage of images. As an example, the camera 15 may be a commercial CCD camera such as the Watec model 902 with 1" camera lens. The applied RF signal is obtained from a computer-controlled RF controller and the LCVR applied voltage is obtained from an LCVR controller which may also be controlled from a computer 30. As an example, the liquid crystal variable retarder (LCVR), used to change incident polarization, can collect both spectral and polarization signatures under computer control and may have a range of 400-800 nm, passband 10 nm @600 nm, a weight of less than 5 lb, and a size of approximately 8×6×4 inch. Further descriptive material is found in N. Gupta, et al., "Acousto-optic tunable filter based visible-to near-infrared spectropolarimetric imager," Opt. Eng. 41, 1033-1038 (2002)), hereby incorporated by reference.

The utilized AOTF 12 was essentially a real-time programmable solid-state no-moving-parts optical device which performs both filtering and dispersing operations (see N. Gupta, "Acousto-Optic Tunable Filters," Opt. Photon. News 8, 23-27 (1997) and M. S. Gottlieb, "Design and Fabrication of Acousto-Optic Devices," Chap. 4 in Designing and Fabrication of Acousto-Optic Devices, A. Goutzoulis and D. Pape, Eds., pp. 197-283, Marcel Dekker, New York: (1994)). An AOTF is fabricated as a specially cut prism in a single crystal of birefringent material which is transparent in the spectral region of interest and has a low acoustic absorption. The crystal is specially cut based on a wide angle Bragg diffraction geometry and both its input and output facets are antireflection coated. The crystal geometry is chosen such that the incident optical beam direction is perpendicular to the input facet. A piezoelectric transducer is bonded on one side of the crystal and an acoustic absorber is applied to the opposite side of the transducer. When a radio frequency (rf) signal is applied to the piezoelectric transducer, it converts it into an acoustic shear beam that propagates inside the crystal and sets up regions of high and low densities within the crystal. The propagating acoustic beam is absorbed by the acoustic absorber when it traverses through the crystal. Thus a moving phase grating is set up inside the crystal whose period is given by the wavelength of the acoustic wave in the crystal. This grating can be erased by removing the applied rf or the period of the grating is changed by changing the frequency of the applied rf signal. The light source can be a white light source such a lamp or sunlight. When white light is incident on the input facet of the crystal, it passes only a selected narrow band with the center wavelength inversely proportional to the frequency of the applied rf signal based on principle of conservation of momentum. In other words, the crystal acts as a narrow bandpass filter that can be used to pass light with a single wavelength. Owing to conservation of energy, the frequency of the diffracted light is Doppler shifted, but this frequency shift is insignificant and can be ignored (the frequency of the incident light is a few million times greater than the frequency of the ultrasonic beam). Such an interaction between light and sound is known as inhomogenous Bragg diffraction. The time it takes for the acoustic beam to propagate from the transducer to the absorber is the time it takes to change the passband of the filter. Most AOTFs used in spectral imaging applications use a noncollinear geometry in designing an AOTF cell which uses a wide angle Bragg interaction geometry based on the symmetry properties of the anisotropic crystal under consideration.

Figure 3:
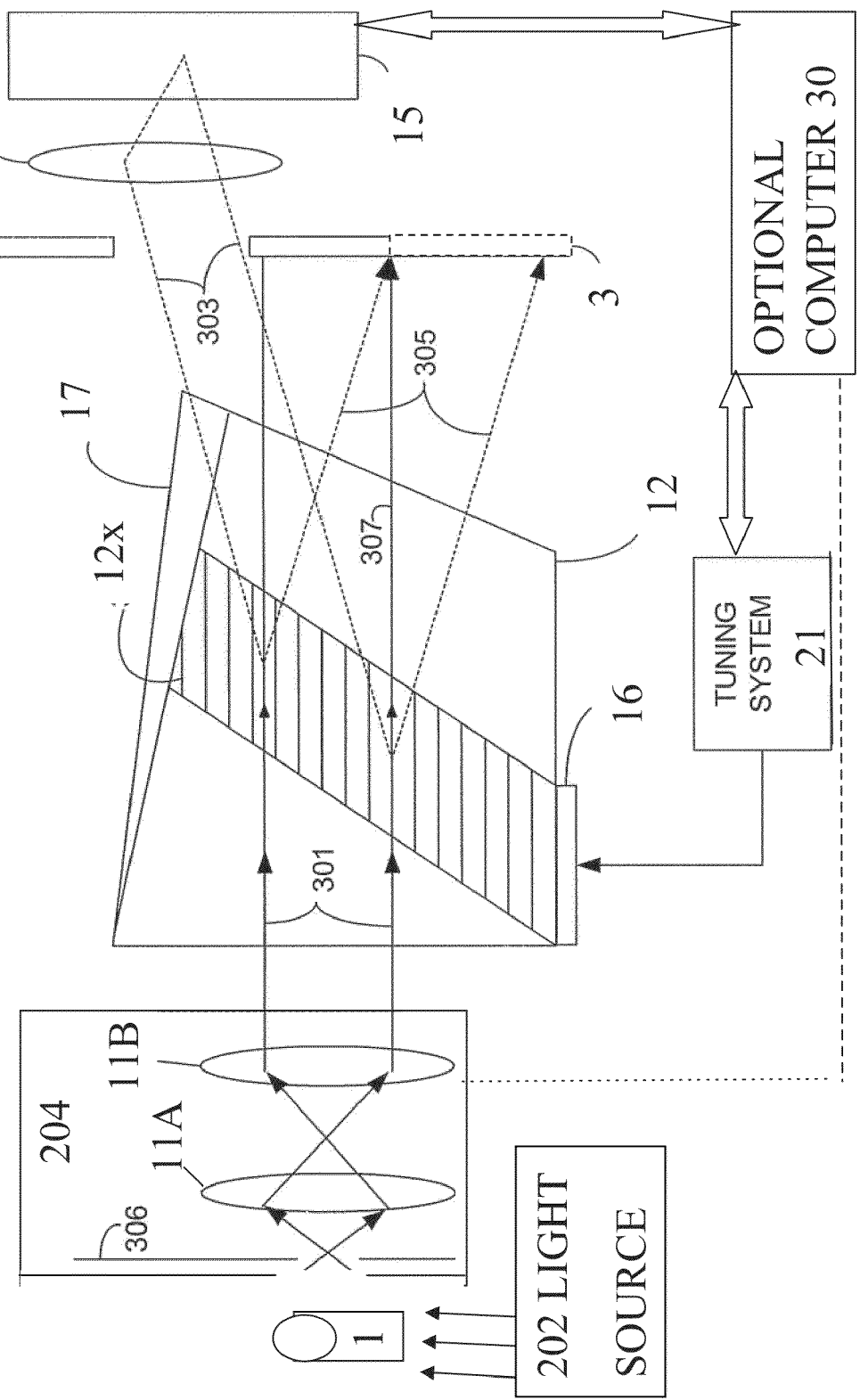
FIG. 3 is a schematic diagram of a preferred embodiment of a hyperspectral scene projection/generation system 10A comprising a light source, an optic system 204, and a tunable dispersive device 12 (comprising an acousto-optic tunable filter with a transducer 16 and absorber 17).
Figure 4:
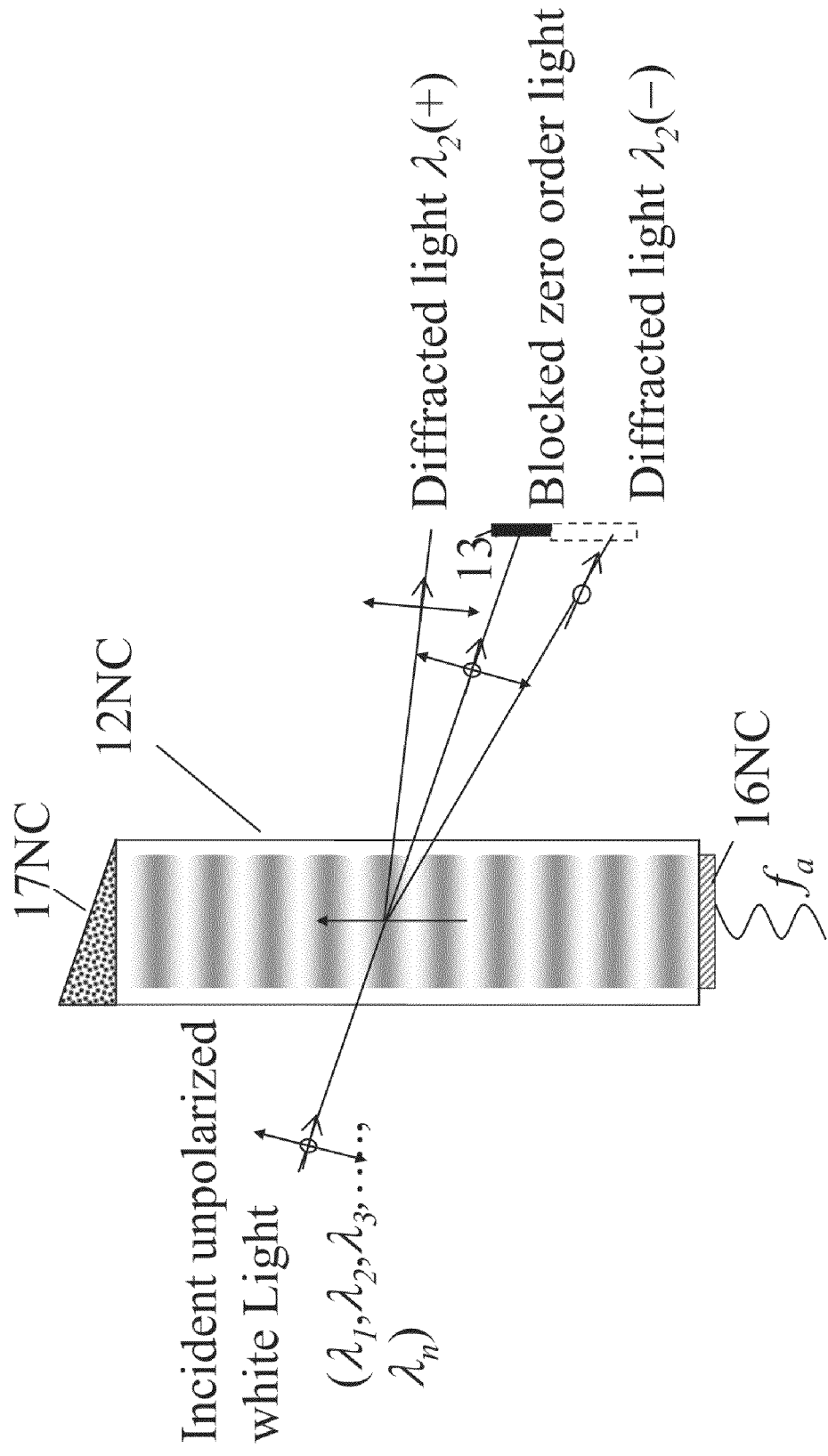
FIG. 4 is a schematic diagram of a preferred embodiment of a hyperspectral scene projection/generation system 10B comprising a light source, a tunable dispersive device 12NC (comprising a noncollinear acousto-optic tunable filter with a transducer 16NC and absorber 17NC).

FIG. 3 is a schematic diagram of a preferred embodiment of a hyperspectral scene generation system 10A comprising a light source, an optic system 204, a tunable dispersive device 12 (comprising a noncollinear acousto-optic tunable filter with a transducer 16 and absorber 17), a tuning system 21 that controls the tuning of the dispersive device 12 through a transducer 16, a lens 14, and a display system 15. The light source may be a fiber-optic coupled broadband light as a source. As an example, an acoustooptic tunable filter 12 may be utilized to image different optical colors in the visible wavelength region. The acoustooptic tunable filter 12 may be fabricated in single crystal of tellurium dioxide. Two plano-convex lenses may be used to form a collimated beam. The spectral scene is imaged on a commercial CCD camera that is connected to a frame grabber to digitize the analog output of the camera. The digitized image may be stored on a computer 30. The operation of the acousto-optic tunable filter and camera are automated and/or may be controlled by a computer 30. The radio frequency signal applied to the imager may also be controlled from the same software as the imager, optionally contained on computer 30. As depicted in FIG. 3, the imager shown uses one of the diffracted beams and blocks the undiffracted beams. The other diffracted beam may be blocked as well as shown by the dotted block.

For AOTF tuning, diffracted wavelength $\lambda_o$ depends on crystal birefringence, acoustic velocity, angle of light incidence, and applied radio frequency; related as follows:

$$\lambda_0 = \frac{\Delta n V}{f_a}[\sin^2 2\theta_i + \sin^4\theta_i]^{1/2}$$

Spectral resolution depends on diffracted wavelength, length of acousto-optic interaction, birefringence, and angle of light incidence, related as follows:

$$\frac{\Delta\lambda}{\lambda_0} = \frac{0.9\lambda_0}{L\Delta n \sin^2\theta_i} \equiv \frac{1}{R}$$

Optionally, the light source can comprise a two-dimensional broadband light source, which covers the electromagnetic spectrum from ultraviolet (UV) to infrared (IR). In some embodiments, a light source can be used where only a portion of the UV to IR range is covered or a different electromagnetic range is covered. The light source 202 can be a white light source. Other configurations for the light source 202 can be used, including a 2-D resistor array of elements, where each element can be heated under individual control to emit infrared light, a micro-mirror device with a 2-D structure, where each mirror can be controlled separately, or light emitting diodes. Regardless of the light source embodiment used, each of the light sources may be operated with or without computer control. For example, if you utilize three light sources having wavelengths of approximately 540, 560 and roughly 580 (577 nm), the illumination could be accomplished to compare returns and analyze the subject as to whether the subject is oxygenated or deoxygenated.

The optic system 204 may comprise one or more filters and lenses. The optic system 204 receives the light from the light source 202, and in one embodiment, collimates the received light. The collimated beam of light is filtered and provided to the dispersive device 12. In some embodiments, non-collimated beams may be generated and processed.

The dispersive device 12 is coupled to the tuning system 214 through a transducer 16. The transducer 216 may be, for example, a thin plate piezoelectric transducer. The tuning system 214 provides an adjustable radio frequency (RF) signal to the transducer 216, which converts the signal to sound waves. The sound waves cause dispersion of the collimated beam provided by the optic system 204, resulting in the production of beams of light at distinct wavelengths. The tuning system 21 may comprise a computer or other processing device, control software, and/or an RF generator. Through application of an adjustable RF signal to the transducer 16 coupled to the dispersive device 12, the wavelength of the spectral image of the scene generated on the display system 15 can be changed. In other words, all the radio frequency change operations can be done seamlessly under computer control, locally or from a remote location. In some embodiments, manual adjustment can be used in addition to or in lieu of automatic control. Further, in response to either manual input or in response to instructions from control software, the tuning system 14 can provide sequential changes or random changes (or a combination of both) to the frequency signal.

In one embodiment, the dispersive device 12 comprises a non-collinear, acousto-optic tunable spectral filter. The dispersive device 12 may also comprise an aperture, among other elements. Other dispersive devices that are tunable and produce regions of high and low density (e.g., compression and rarefaction) to produce a grating (e.g., phase grating) effect based on the tuning signal can be used to obtain images of full 2-D spectral scenes, including liquid crystal light filters, Fabry-Perot interferometers, Michaelson interferometers, or diffractive optical lenses, among other devices.

The light output from the dispersive device 12 at a distinct wavelength passes through the lens 14 (e.g., an iris lens) and is imaged onto and/or in the display system 15. The display system 15 may comprise a projection screen, video monitor, computer, and/or a 2-D detector array (e.g., as provided in a camera). For example, the display system 15 may comprise a charge-coupled device (CCD) camera and a computer. The CCD camera may be coupled to a frame grabber to digitize the analog output of the camera, and the digitized images can be stored on a computer. The operation of the dispersive device 12 and/or display system 15 may be manually operated or automated, or a combination of both forms of control.

It will be understood that the hyperspectral scene generation system 10A illustrated in FIG. 3 provides an overview of an exemplary embodiment of a hyperspectral scene projection/generation system 10A, and in some embodiments may include fewer, greater, and/or different components.

In the preferred embodiment depicted in FIG. 5, a compact, portable, agile spectropolarimetric VNIR imager was used with an AOTF 12 for the light dispersive element in combination with LCVR 13 for polarization selection and a CCD camera to cover the spectral range of operation.

The imager was used to carry out some passive imaging experiments using a human subject to evaluate the imaging capabilities in detecting oxygenated versus deoxygenated blood by constricting the blood flow—(i) in a finger by wrapping a tight rubber band around the finger and (ii) in the lower arm by using a pressure cuff on the upper arm. The subject was located approximately two meters away from the imager. After collecting an image cube and analyzing it using hyperspectral image processing software, the effects of skin deoxygenation was observed both in the constricted finger and the arm.

The imager was used in a passive mode from 400 to 800 nm with a 10-nm interval to acquire spectral images at 41 bands with polarization settings of 0° and 90° at each wavelength corresponding to the horizontal and the vertical polarizations of the reflected light from a human hand and arm illuminated by an ordinary white light source. Although 41 bands were selected, any number of bands could be utilized depending upon the circumstances and accuracy desired. The hand and arm were located two meters from the camera. Two separate experiments were performed: first for imaging the hand with the index finger constricted by a rubber band wrapped around it and the second for imaging the lower arm when the upper arm was constricted by a pressure cuff. The spectral analysis was performed using ENVI (registered trademark), but one of ordinary skill in the art would readily appreciate that other procedures could be utilized with comparable results.

For each imaged object two separate image cubes each with 41 bands were obtained corresponding to the two orthogonal polarizations of the light reflected from the illuminated object. A diffuse white board was also imaged and was used to normalize the data. The spectral plots clearly showed the two peaks corresponding to the oxygenated skin for the unconstructed finger due to oxyhemoglobin (corresponding to 540 and 577 nm) and the single peak due to deoxyhemoglobin (corresponding to 559 nm) for the constricted index finger and the lower arm. An ordinary white light source was used to illuminate the objects and the images were collected from a distance of two meters with no prior sample preparation; the results showed the effect of oxygenation and deoxygenation for a live human subject.

Higher image contrast can be achieved by using both spectral and polarization signatures. Spectral features arise due to the material properties of objects, as a result of the emission, reflection, and absorption of light. The polarization features arise from the physical nature of the object including surface roughness and subsurface scattering. Using a hyperspectral imager, one can acquire an image cube that consists of a number of spectral images of the same scene taken at a number of narrow spectral bands. Spectral signatures from each pixel can be easily extracted and used to obtain the characteristic spectral signatures of different materials that make up objects and backgrounds in the scene or subject of interest.

FIGS. 2 and 3 show the propagation of light and sound waves in a noncollinear AOTF cell. The filter design is based on the consideration that for a spectral imaging instrument and a fairly broad bandpass is needed and a large linear as well as angular aperture such that there is a substantial light throughput. In FIG. 2, the filtering operation of a noncollinear AOTF is shown with the transducer and absorber. When unpolarized white light is incident on the input facet, it gets diffracted by the traveling grating set up in the crystal by the acoustic wave. The two orthogonally polarized diffracted light beams 1 and 2 at a wavelength inversely proportional to the applied rf, are coming out at an angle to the incident beam. The zero order beams contain all wavelengths except the one that was diffracted by the traveling grating. The period of the traveling grating is given by the wavelength of the acoustic wave in the crystal and can be changed by changing the applied rf. Only one of the diffracted beams is used for imaging by blocking the rest of the beams.

An AOTF imager designed in accordance with the principles of the present invention uses the concept that for an unpolarized incident light, a noncollinear AOTF has two diffracted beams, along with two orthogonally polarized undiffracted beams that contain all the incident wavelengths minus the one that is diffracted. The advantages of an AOTF include light weight, compact, electronic tuning, lack of moving parts, low drive power, rapid tuning and scanning (100,000 frames/sec), high spectral resolution, broad tuning range, RF-driven and remote control operation; sequential or random or multi wavelength access; and polarization separation.

A preferred embodiment imager design uses one of the diffracted beams and blocks the other diffracted beam as well as the undiffracted beams as shown in FIG. 2. Diffracted wavelength depends on crystal birefringence, acoustic velocity, angle of light incidence, and applied radio frequency:

The tuning relationship and the spectral resolution for a noncollinear filter, using wide-angle diffraction geometry, can be approximated by the following two equations. In the first equation, diffracted wavelength depends on crystal birefringence, acoustic velocity, angle of light incidence, and applied radio frequency. In the second equation, spectral resolution depends on diffracted wavelength, length of acousto-optic interaction, birefringence, and angle of light incidence.

$$\lambda_0 = \frac{\Delta n V}{f_a}[\sin^2 2\theta_i + \sin^4 \theta_i]^{1/2} \quad (1)$$

$$\frac{\Delta\lambda}{\lambda_0} = \frac{0.9\lambda_0}{L\Delta n \sin^2 \theta_i} \equiv \frac{1}{R} \quad (2)$$

where $\lambda_0$ is the diffracted optical wavelength, $\Delta n$ is the birefringence of the material (difference of two refractive indices), V is the acoustic velocity in the material, fa is the applied rf signal (same as the acoustic frequency), $\theta_i$ is the optical angle of incidence with respect to the crystal optic axis, L is the length of AO interaction in the crystal (same as the length of the transducer), $\Delta\lambda$ is the optical passband, and R is the spectral resolution. It is clear from Eq. (1) that the optical wavelength can be changed by changing applied rf because $\lambda_0$ increases as fa decreases or vice versa. To obtain polarization information, as shown in FIG. 5, a spectrally tunable commercial LCVR 13 is placed in front of the AOTF, and uses two retardance values corresponding to the horizontal and vertical polarizations for each diffracted wavelength. The tuning of such a retarder is done by changing the applied voltage. An LCVR is a device that is made of a thin layer of a nematic liquid crystal between two parallel glass windows spaced a few microns apart. The retardance or the phase shift between the two orthogonally linearly polarized components of transmitted light by LCVR is obtained by applying a low voltage waveform to the liquid crystal layer. See, "Stokes polarimetry using liquid crystal variable retarders," Meadowlark Optics, Inc. (2005). URL http://www.meadowlark.com, hereby incorporated by reference as though fully rewritten herein. The specifications of the LCVR may be, for example, a Nematic LC thin film, with a range 0.4-1.8 mm.

Figure 9:
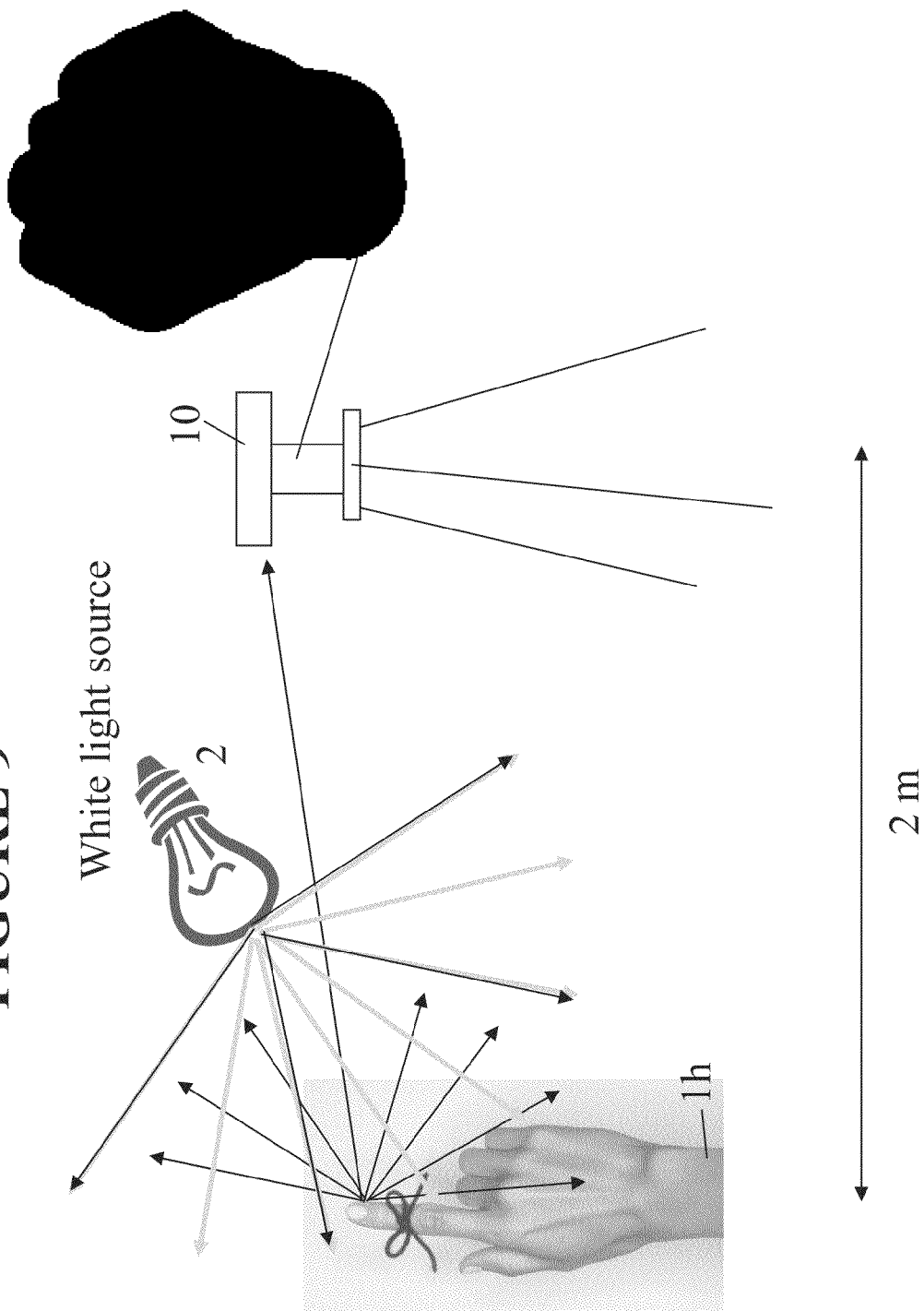
FIG. 9 schematically depicts an experimental set-up for an AOTF imager optical package system used in conjunction with a hand.

Variable retardance can be obtained by varying the applied voltage. A graph of the retardance as a function of voltage is shown in FIG. 8. For each wavelength, two different values of voltage are used corresponding to zero and quarter wave retardances to obtain images with two orthogonal polarizations. The values of these two retardances vary as a function of wavelength and corresponding plots can be obtained from the vendor. A preferred embodiment ATOF assembly may optionally comprise a small black box mounted on a tripod as depicted in FIG. 9. As depicted in FIG. 5, the light from the scene is first incident on the first iris which defines the angular aperture of the AOTF. Next, the light passes through an LCVR where a retardance is applied to it as discussed above. The light transmitted from the LCVR is next imaged inside the AOTF cell by the first plano convex lens and after the AOTF only one of the two diffracted beams from the AOTF is imaged on the CCD camera using the combination of the second plano convex lens, second iris 12 and the camera lens. The two plane mirrors M1 and M2 are mounted on the tilt plates that are used to fold the optical path in order for the optical package to fit inside a small box. By tuning the filtered wavelength over the entire tuning range, two separate hyperspectral image cubes can be acquired corresponding to the two orthogonal polarizations. Since both the retarder and the AOTF are tuned electronically, no moving parts are involved, and the imager is adaptive and robust as compared to other traditional hyperspectral imagers.

The applied radio frequency (RF) signal for the LCVR is obtained from a computer-controlled rf controller and the LCVR applied voltage is obtained from an LCVR controller which is also controlled from a computer. The specifications of the Acousto Optic Filter (AOTF) imager are given in table 1 below.

TABLE 1

Specifications of AOTF Imager

| PARAMETER | VALUE |
| --- | --- |
| AOTF material | $TeO_2$ |
| AOTF input aperture | $15 \times 15$ mm$^{22}$ |
| AOTF angular aperture | 4.2° |
| AOTF spectral range of operation | 400-800 nm |
| Applied rf range | 120-150 MHz |
| Spectral resolution | 10 nm @600 nm |
| LCVR material | Nematic liquid crystal |
| LCVR diameter | 2.5 cm |

TABLE 1-continued

Specifications of AOTF Imager

| PARAMETER | VALUE |
| --- | --- |
| LCVR voltage range | 0-20 V |
| LCVR spectral range | 400-1800 nm |
| Image size | 640 × 480 pixels |

I. Experimental Procedure

The present invention may be utilized to find out if a person's blood is oxygenated or deoxygenated by using remotely captured hyperspectral images of a person's arm or other body parts by using an acousto-optic based hyperspectral imager operating from 400 to 800 nm. The light from a fiber optic coupled source is illuminated on a person's body part and then spectral images are captured using an automated hyperspectral imager. In order to recreate a deoxygenated arm, the arm or the other body part is put under pressure to reduce the oxygen level in the blood and spectral images are captured. A diffuse white board sitting at the same position as the arm or other body part is then imaged with same illumination. Hyperspectral image cubes were generated using a commercial hyperspectral software package and spectrum of a point on the arm was extracted and normalized using the spectrum from the white board. This effectively cancels out the spectral response of the light source and the imager. When the spectrum from the arm under pressure are examined, it clearly shows that the blood is deoxygenated while similar data from the arm under normal condition shows that the blood is oxygenated. The same or similar procedure could be useful in a hostile or battlefield scenario to remotely determine if an individual is alive or dead without touching his or her body to determine his pulse. This would avoid others from exposure to chemical and biological agents if the person in question was exposed to them in a hostile environment.

Experiments were conducted to assess the ability of a preferred embodiment spectropolarimetric imager with respect to measurement of oxygen saturation ($SO_2$) in the skin. Two spectral imaging experiments were carried out to obtain image cubes using a VNIR imager to image (i) a hand and (ii) arm of a human subject located two meters away from the imager. Also recorded were image cubes of a diffuse white board to normalize the images obtained from the hand and arm.

In a first experiment an ordinary white light lamp source was used to illuminate the hand of a volunteer. Passively imaged diffuse reflection from live human subject skin was conducted at a range of 2 meters using ordinary unpolarized white light source.

In the first experiment, a rubber band was tied on the index finger of the individual to interrupt the flow of oxygenated blood to that area. In the second experiment with the arm, a pressure cuff was applied to the upper arm of the subject that was also illuminated by the same white light source as in the first experiment and the forearm and hand were imaged. Images were recorded from 400 nm to 800 nm with a 10 nm spectral interval. Images were acquired before and after ~5 minute blood constriction. Two separate image cubes each with 41 spectral images corresponding to two orthogonal polarizations were recorded for each object. The wavelength was changed by varying the applied rf between 50 and 120 MHz to correspond to the desired optical wavelength range. The rf signal power used was less than 1.0 W. Each spectral image was recorded with two orthogonal polarizations of the light incident on the imager. Both the rf synthesizer and the LCVR were controlled using a personal computer. The CCD output was captured and digitized using a frame grabber and stored on the computer hard drive. The size of each stored image was 640×480 pixels. A custom designed graphical user interface was used for a seamless operation of the imager.

II. Experimental Results and Analysis

Some examples of the spectropolarimetric images obtained with an imager constructed with the principles of the present invention and used in the experiment are presented.

FIG. 10 illustrates how images of a hand and arm can be collected with rubber band on the index finger were collected. Shown in FIG. 10 are three spectral images collected with horizontal polarization. The top of FIG. 10 shows three examples of reflected spectral images (taken using light having wavelengths of approximately 540 nm, 560 nm and 580 nm) of a human hand (collected with rubber band on the index finger) and the bottom shows similar images (taken using light having wavelengths of approximately 540 nm, 560 nm and 580 nm) for lower arm collected with horizontal polarization.

The wavelength dependence of the skin reflectance may be analyzed using a computer program such as ENVI (trademark). Two regions of interest (30×30 pixels each) were selected on a constricted finger and on an un-constricted finger. Absorbance in each location was calculated after normalizing the skin values by our reflectance standard (white board) using Eq 3.

$$A = -\log_{10}\left(\frac{R_{skin}}{R_{board}}\right) \quad (3)$$

Typical results for the finger experiment are illustrated in FIG. 13. The absorbance spectrum on the unconstructed finger is typical of oxygenated hemoglobin with two visible peaks at 540 nm and 577 nm. For the constricted finger these peaks have disappeared and are replaced by a large peak centered around 559 nm.

Figure 14:
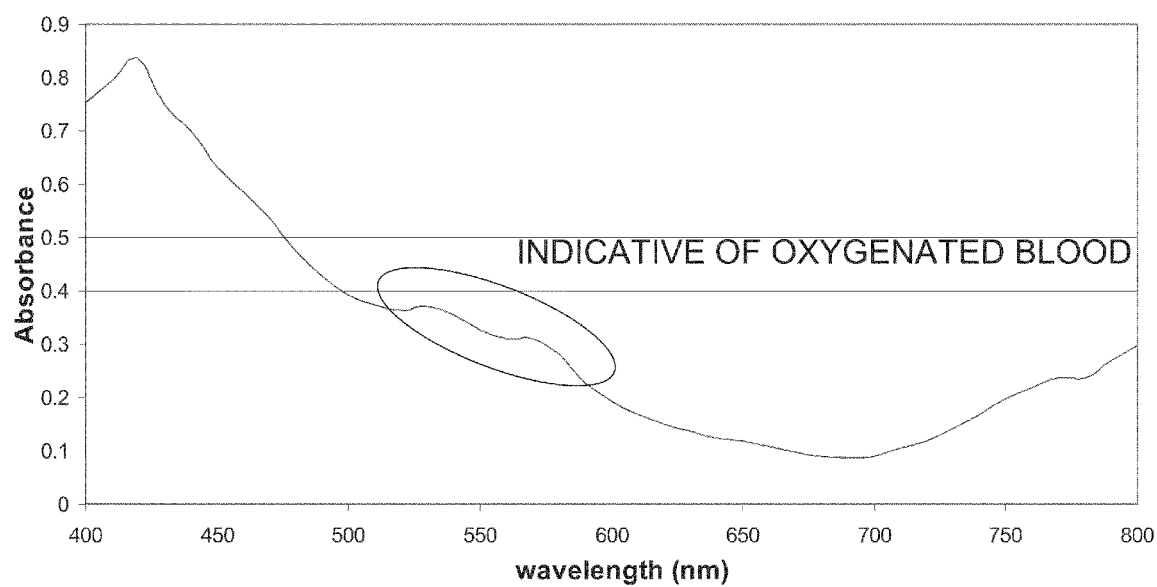
FIG. 14 is a graphical illustration for oxygenated blood representing spectra (with horizontal polarization) obtained from image cubes in which absorbance is plotted as a function of wavelength of light in nanometers.

FIGS. 14 through 16 are graphical illustration of the mean of regions of interest captured on a constricted finger and on an unconstricted finger (circles). The data was normalized by the respective 420 nm value for both curves. Oxygen saturation in both regions of interest was calculated using an algorithm first proposed by N. Kollias, A H Baqer, "Quantitative assessment of UV-induced pigmentation and erythema," Photodermatol. 1988; 5, pp. 53-60, (hereby incorporated by reference) which takes into account the effect of melanin absorption by subtracting its contribution from the general data Skin pigmentation is approximated as the slope of a fitted straight line between the values of absorbance at 620 nm and 720 nm, the absorbance curve of melanin decreasing monotonically between 600 and 750 nm. Oxygen saturation is calculated by using tabulated absorption curves of oxygenated and deoxygenated hemoglobin to fit the experimental data in the range 550 to 580 nm. Oxygen saturation in the un-constricted finger was close to 60% while in the constricted finger values around 1% were obtained. These values agree with the one obtained by other groups with different experimental techniques and algorithms as discussed in N. Kollias, A H Baqer, "Quantitative assessment of UV-induced pigmentation and erythema," Photodermatol. 1988; 5, pp. 53-60, and M. P. Siegel, Y. L. Kim, H. K. Roy, R. K. Wali, V. Backman, "Assessment of blood supply in superficial tissue by polarization-gated elastic light-scattering spectroscopy," 45, Appl. Optics, 2006, both of which are hereby incorporated by reference. Skin oxygen saturation is expected to vary between 50% and 70% due to the spatial micro non-uniformity of $SO_2$ (oxygen saturation) in the skin layers. Values collected on the forearm yielded similar results, $SO_2$ was ~50% before the pressure cuff was put in place and plummeted to 0% after a few minutes of vasoconstriction. Since the light source was unpolarized, no polarization gating was obtained from the reflected images.

A compact, portable, agile spectropolarimetric VNIR imager was used with an AOTF for the light dispersive element in combination with LCVR for polarization selection and a CCD camera to cover the spectral range of operation. This imager was used in a passive mode from 400 to 800 nm with a 10-nm interval to acquire spectral images at 41 bands with polarization settings of 0° and 90° at each wavelength corresponding to the horizontal and the vertical polarizations of the reflected light from a human hand and arm illuminated by an ordinary white light source. The hand and arm were located two meters from the camera. However, other distances could be utilized without departing from the spirit of the invention. Two separate experiments were performed: first for imaging the hand with the index finger constricted by a rubber band wrapped around it and the second for imaging the lower arm when the upper arm was constricted by a pressure cuff. The spectral analysis was performed using Matlab.

For each imaged object two separate image cubes each with 41 bands were obtained corresponding to the two orthogonal polarizations of the light reflected from the illuminated object. A diffuse white board was also imaged and was used to normalize the data. The spectral plots clearly showed the two peaks corresponding to the oxygenated skin for the unconstructed finger due to oxyhemoglobin (corresponding to 540 and 577 nm) and the single peak due to deoxyhemoglobin (corresponding to 559 nm) for the constricted index finger and the lower arm. Considering that an ordinary white light source was used to illuminate the objects and the images were collected from a distance of two meter with no prior sample preparation, these results are rather remarkable in showing the effect of oxygenation and deoxygenation for a live human subject. Further work may provide enhanced sensitivity. Based on the results, it should be noted that a prototype AOTF-based imager which was developed for military applications provides a useful tool for data acquisition for biomedical applications in either hyperspectral or spectropolarimetric modes because such imagers are compact and agile with no-moving parts and have automated operation and are easy to use.

FIG. 11 illustrates image acquisition and analysis using a preferred embodiment of the present invention comprising the steps of collecting spectral images at same polarization, form an image cube using the spectral images; extract a spectral profile across the cube, and obtaining normalized absorbance wrt reference. As shown at the bottom right of FIG. 11, oxygenated blood contained a "valley" in the graphical representation which correlates to the absorption by oxygen in the blood at the given wavelength.

Experiments were conducted and video/photographs taken to produce spectral images in each image cube from 800 to 400 nm of constricted human body components; the left image being a hand with a constricted finger and the right image being a constricted arm with a pressure cuff. For example, a video of 41 sequential frames could be used to produce an image "cube" with 41 frames, as schematically shown in FIG. 11.

FIG. 12 depicts skin analysis conducted in accordance with the principles of the present invention. As seen in the graph in FIG. 12, the unconstricted finger gives typical two visible peaks at 540 nm and 577 nm corresponding to oxygenated hemoglobin. The constricted finger has a large peak centered around 559 nm corresponding to deoxyhemoglobin. Similar results were obtained for constricted arm. Oxygen saturation in the unconstricted finger was close to 60% and 1% for the constricted finger using Kollias algorithm, similar results obtained for arm. No polarization gating was observed due to the use of unpolarized light. As seen in FIG. 12, the procedure entailed the steps of extracting the spectral profiles, computing equation 3 (also shown in FIG. 12):

$$A = -\log_{10}\left(\frac{R_{skin}}{R_{board}}\right)$$

and normalizing to A@420 nm.

FIG. 13 is a graphical presentation illustrating a normalized spectral absorbance showing a comparison of constricted/restricted and nonconstricted/unrestricted finger skin with the absorbance spectrum for an unconstricted finger typical of oxygenated hemoglobin having 2 visible peaks at 540 nm and 577 nm. For a constricted finger these peaks disappear, and a single large peak centered @ 559 nm for deoxyhemoglobin appears.

FIG. 14 is a graphical illustration representing spectra (with horizontal polarization) obtained from image cubes in which absorbance is plotted as a function of wavelength of light in nanometers. The portion indicative of oxygenated blood is circled. The data shown was not normalized with absorbance value at 420 nm.

FIG. 15 is a graphical illustration representing deoxygenated blood (obtained using a rubber banded index finger) with a spectral plot obtained from image cubes in which absorbance is plotted as a function of wavelength of light in nanometers (with horizontal polarization). The data is not normalized with absorbance value at 420 nm.

FIG. 16 is a graphical illustration representing deoxygenated blood (obtained using a lower arm) with a spectral plot obtained from image cubes in which absorbance is plotted as a function of wavelength of light in nanometers (with horizontal polarization). The data is not normalized with absorbance value at 420 nm.

Although the preferred embodiments were discussed in relation to determining oxygen content, other chemicals could be detected using the principles of the present invention. For example, for oxygen satuaration ($SO_2$) measurement, using the algorithm described in Kollias et al., the effect of melanin can be "subtracted" by fitting the curve is between 620-720 nm. The $SO_2$ may then be calculated by fitting a curve between 550 and 580 nm. The $SO_2$ value obtained for unconstricted finger was a 60% $SO_2$ value, while for constricted finger the value was 1%. Similar comparison values can be obtained using the forearm.

As stated in the foregoing, the present invention is directed to the detection of elements and/or chemicals such as an oxygen deficiency in the blood or hypoxia in a subject body. Causative factors such as drowning, strangling, choking, suffocation, cardiac arrest, head trauma, and carbon monoxide poisoning can create conditions leading to cerebral hypoxia, which can lead to coma, seizures, and even brain death. Similarly, carbon monoxide and cyanide poisoning may lead to histotoxic hypoxia, which is the inability of body tissues to use oxygen. Also, certain narcotics will prevent oxygen use by the tissues. The present invention may be used to monitor, screen, or detect the lack of the presence of oxygen in body tissue of subject individuals which may be indicative of poisoning, chemicals, or certain narcotic usage. For a more detailed example of screening systems, see U.S. Pat. No. 7,141,786, hereby incorporated by reference. Moreover, the invention is particularly suitable for persons or subjects with injuries, such as gangrene, whether the individual would be subjected to a great deal of pain if subjected to contemporary diagnostic instruments. Since the present invention may be operated at a distance from the subject's skin, no pain would be encountered.

The invention may prove useful in the analysis of bruises on the body which are otherwise not visible which appear when comparing spectral images taken at two orthogonal polarizations. For example, such analysis could prove useful when a coroner wants to asses whether or not a baby has been badly bruised. Such bruises may become evident only when the subject is imaged by a modified form of the invention utilizing light. The polarization difference image would provide the shape of the bruise for discernment as to the cause of the bruise. In addition, the present invention could prove useful in the cosmetic industry for the analysis of make-up products; particularly in conjunction with a polarization varying embodiment of the present invention. For example, using polarized light, light which is reflected from the surface contains information about the different contours; i.e. bruises. In analyzing the effectiveness of make-up cosmetics, spectral and polarization may also enhance the effectiveness of the analysis of the cosmetic products.

It should be emphasized that the above-described embodiments are merely possible examples of implementations. Many variations and modifications may be made to the above-described embodiments. All such modifications and variations are intended to be included herein within the scope of the disclosure and protected by the following claims. The term "processor" or "computer" as used herein includes multiprocessors, computers, supercomputers, data processor, laptops, signal processors, personal computers, notebook computers, and/or any component which processes data. The term "image generator" as used herein includes a "processor" or "computer" which generate images and/or any element or component, including components within a processor, which generate images, including a display, screen or monitor. The abbreviation RF or rf is used for radio frequency or a radio frequency signal. The terminology "chemical" as used herein means solid, liquid, or gas and includes substances, additives, stimulants, narcotics, agents, toxins, and/or reagents. The term "subject" as used herein means a human, animal, organ, body part, skin, non-plant organisms, or animal biological matter. As used in the following claims, the terminology "images" or "spectral images" relates to the information collected by hyperspectral sensors as a set of "images" with each image representing a range of the electromagnetic spectrum, also known as a spectral band. As used herein the terminology "image cube" or "hyperspectral image cube" refers to the combination of "hyperspectral images" to form a hyperspectral cube for processing and analysis. As used herein, the terminology $SO_2$ means oxygen saturation (not sulfur dioxide).

The invention claimed is:
1. A method of detecting oxygen content in a human being comprising
  generating a plurality of spectral images of a human being using an automated hyperspectral imager,
  determining from the at least one spectral image the relative oxygen content of the human being for the purposes of drug testing, the relative oxygen content in the human's blood being approximated by comparing the spectral images of the subject to reference spectral images to determine whether the human being has taken an illicit drug.

2. The method of claim 1 wherein the drug to be detected is a narcotic and wherein the step of generating a plurality of spectral images of the human being comprises generating at least one spectral image of a reference subject at substantially the same position as the human being with substantially the same illumination using an automated hyperspectral imager.

3. The method of claim 2 further comprising generating hyperspectral image cubes such that the spectrum of the body part is extracted and normalized using the spectrum from the reference object to cancel out the spectral response of the light source and the imager.

4. The method of claim 3 wherein the step of comparing spectral comprises observing spectral from the human in comparison with at least one reference image under normal conditions; thereby revealing whether or not the blood is oxygenated or deoxygenated.

5. The method of claim 4 wherein the spectral of the human body part are plotted graphically and oxygen saturation is calculated by using tabulated absorption curves of oxygenated and deoxygenated blood to fit the experimental data in the range approximately 550 to 580 nm.

6. The method of claim 5 wherein spectral plots comprising peaks at approximately 540 and 577 nm indicate of absorption by oxyhemoglobin found in oxygenated blood; and spectral plots comprising a single peak at approximately 559 nm indicate a deficiency of oxygen in the blood.

7. The method of claim 1 wherein the step of generating at least one spectral images is accomplished using an automated acousto optical tunable filter.

8. The method of claim 7 wherein the automated acousto optical tunable filter is polarization sensitive to obtain higher image contrast.

9. The method of claim 1 further comprising the step of extracting spectral signatures from pixels of the spectral image to obtain characteristic spectral signatures of different materials making up the human being.

10. The method of claim 1 wherein the measure of oxygen deficiency in the blood is an in indicator of hypoxia oxygen deficiency.

11. The method of claim 1 wherein the spectral images are obtained using an electrically tunable optical filter system comprising a moving diffraction grating set up in an anisotropic crystal by propagating sound waves generated from an applied RF signal.

12. A method of remote drug testing by determining the level of oxygenation of the blood of a subject comprising:
  generating at least one spectral image of the subject utilizing an automated hyperspectral imager;
  determining from the at least one spectral image the oxygen content of the subject located at least two meters away from the imager to determine whether or not the subject has taken an illicit drug.

13. The method of claim 12 further comprising the step of generating at least one spectral image of a reference object; and wherein the step of generating at least one spectral image of the subject comprises generating a plurality of spectral images using the automated hyperspectral imager.

14. The method of claim 13 wherein the step of generating at least one spectral image of a reference object comprises generating at least one spectral image of a reference subject at substantially the same position as the subject with substantially the same illumination using the automated hyperspectral imager.

15. The method of claim 14 further comprising generating hyperspectral image cubes such that the spectrum of the body part is extracted and normalized using the spectrum from the reference object to cancel out the spectral response of the light source and the automated hyperspectral imager.

16. A system for determining whether or not a person has taken an illicit drug based upon the level of oxygenation of the blood of a human body part comprising:
- a hyperspectral image generator for generating a plurality of spectral images;
- an image capture device for capturing the spectral images;
- a processor for generating hyperspectral image cubes such that the spectrum of the body part is extracted and normalized using the spectrum from a reference object to cancel out the spectral response of the light source and the imager; said processor comparing spectral from a subject image to reference images to thereby reveal the relative oxygen content of the subject in order to determine whether or not the person has taken an illicit drug.

17. The system of claim 16 wherein the hyperspectral imaging system 10 comprises lenses to collimate the light beam, a single color diffracted light camera, and an acousto-optic tunable filter that uses radio waves to filter white light into different colors of diffracted light, the acousto-optic tunable filter comprising a specially cut birefringent crystal prism on which a thin plate piezoelectric transducer is bonded on one side of the crystal and an acoustic absorber on the opposite facet such that when a radio frequency wave is applied to the thin plate piezoelectric transducer, an ultrasonic wave is generated which travels through the crystal and gets absorbed at the other end by the acoustic absorber, whereby the traveling sound wave in the crystal acts like a grating and light gets diffracted in an anisotropic diffraction process.

* * * * *